United States Patent
Marco Colas et al.

(10) Patent No.: US 10,422,791 B2
(45) Date of Patent: Sep. 24, 2019

(54) **HAPTENS AND CONJUGATES DERIVED FROM PYOCYANIN, ANTIBODIES THEREOF, AND IMMUNOCHEMICAL METHOD FOR DETECTING INFECTIONS CAUSED BY *PSEUDOMONAS AERUGINOSA***

(71) Applicants: Consejo Superior De Investagaciones Cientificas (CSIC), Madrid (ES); Centro De Investigacion Biomedica En Red (CIBER), Madrid (ES); Universidad Autonoma De Barcelona, Barcelona (ES)

(72) Inventors: Maria Pilar Marco Colas, Madrid (ES); Nuria Pascual Duran, Madrid (ES); Carme Pastells Diez, Madrid (ES); Francisco Sanchez Baeza, Madrid (ES); Antonio Pedro Villaverde Corrales, Barcelona (ES); Escarlata Rodriguez Carmona, Saragossa (ES)

(73) Assignees: CONSEJO SUPERIOR DE INVESTIGACIONES CIENTIFICAS (CSIS) (ES); CENTRO DE INVESTIGACION BIOMEDICA EN RED (CIBER) (ES); UNIVERSIDAD AUTONOMA DE BARCELONA (ES)

(*) Notice: Subject to any disclaimer, the term of this patent is extended or adjusted under 35 U.S.C. 154(b) by 472 days.

(21) Appl. No.: 14/773,083

(22) PCT Filed: Mar. 4, 2014

(86) PCT No.: PCT/ES2014/070161
§ 371 (c)(1),
(2) Date: Sep. 4, 2015

(87) PCT Pub. No.: WO2014/135730
PCT Pub. Date: Sep. 12, 2014

(65) Prior Publication Data
US 2016/0033489 A1     Feb. 4, 2016

(30) Foreign Application Priority Data
Mar. 5, 2013   (ES) ................... 201330312

(51) Int. Cl.
| | | |
|---|---|---|
| *G01N 33/53* | (2006.01) | |
| *C07K 19/00* | (2006.01) | |
| *C07K 16/44* | (2006.01) | |
| *C07D 241/46* | (2006.01) | |
| *G01N 33/569* | (2006.01) | |

(52) U.S. Cl.
CPC ....... *G01N 33/5308* (2013.01); *C07D 241/46* (2013.01); *C07K 16/44* (2013.01); *C07K 19/00* (2013.01); *G01N 33/56911* (2013.01); *G01N 2333/21* (2013.01); *G01N 2469/10* (2013.01)

(58) Field of Classification Search
CPC ...... C07D 241/46; C07K 16/44; C07K 19/00; G01N 2333/21; G01N 2469/10; G01N 33/5308; G01N 33/56911
See application file for complete search history.

(56) References Cited

U.S. PATENT DOCUMENTS 4,845,222 A     7/1989 Morr et al.

OTHER PUBLICATIONS

Hunter et al., "Phenazine content in the cystic fibrosis respiratory tract negatively correlates with lung function and microbial complexity," Am. J. Respir. Cell Mol. Biol. 2012, 47, No. 6, pp. 738-745; Epub Aug. 3, 2012.*
Wilson et al., "Measurement of Pseudomonas aeruginosa phenazine pigments in sputum and assessment of their contribution to sputum sol toxicity for respiratory epithelium," Infect. Immun., 1988, vol. 56 No. 9, pp. 2515-2517.*
Ahn et al., "An immunoassay for a urinary metabolite as a biomarker of human exposure to the pyrethroid insecticide permethrin," Anal. Bioanal. Chem., 2006, vol. 384, pp. 713-722.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Carme Pastells, Nuria Pascual, Francisco Sanchez-Baeza, and M.-Pilar Marco, "Immunochemical Determination of Pyocyanin and 1-Hydroxyphenazine as Potential Biomarkers of Pseudomonas aeruginosa Infections," Anal. Chem., 2016, vol. 88, No. 3, pp. 1631-1638.*
Kidani, "Synthesis of Phenazine-carboxylic Acids", Chem Pharm Bulletin, 1959, pp. 88-90, vol. 7.
Lau, "The role of pyocyanin in Pseudomonas aeruginosa infection", Trends in Molecular Medicine, 2004, pp. 599-606, vol. 10.
Sharp, "Approaching intelligent infection diagnostics: Carbon fibre sensor for electrochemical pyocyanin detection", Bioelectrochemistry, 2010, pp. 114-119, vol. 77.
Winstanley, "The role of quorum sensing in chronic cystic fibrosis Pseudomonas aeruginosa infections", FEMS Microbiology Letters, 2009, pp. 1-9, vol. 290.
Watson, "Purification and structural analysis of pyocyanin and 1-hydroxyphenazine", European Journal of Biochemistry, 1986, pp. 309-313, vol. 159.
Singh, "Quorum-sensing signals indicate that cystic fibrosis lungs are infected with bacterial biofilms", Nature, 2000, pp. 762-764, vol. 407.
Dietrich, "The phenazine pyocyanin is a terminal signalling factor in the quorum sensing network of Pseudomonas aeruginosa" Molecular Microbiology, 2006, pp. 1308-1321, vol. 61, issue 5.
* cited by examiner

*Primary Examiner* — Galina Yakovleva
(74) *Attorney, Agent, or Firm* — Hayes Soloway PC

(57) ABSTRACT

The present invention relates to a compound of general formula I and to the use thereof as a hapten.

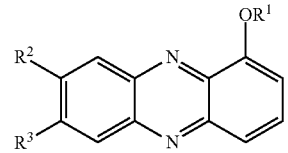

(I)

An object of the present invention is also a conjugate of said compound I with a carrier protein or fragment thereof, with a detectable labelling agent, or with a polymer or support, and to the use thereof for producing antibodies. Furthermore, the present invention also relates to a method for the detection and/or quantification of 1-hydroxyphenazine and/

(Continued)

or pyocyanin using said antibodies and conjugates for the detection of infections caused by *Pseudomonas aeruginosa*.

2 Claims, 2 Drawing Sheets

HAPTENS AND CONJUGATES DERIVED FROM PYOCYANIN, ANTIBODIES THEREOF, AND IMMUNOCHEMICAL METHOD FOR DETECTING INFECTIONS CAUSED BY *PSEUDOMONAS AERUGINOSA*

TECHNICAL FIELD OF THE INVENTION

The present invention relates to compounds of general formula I, to the use thereof as haptens, their conjugates and the use thereof for producing antibodies. Likewise, the invention also relates to a method for the detection and/or quantification of pyocyanin and/or 1-hydroxyphenazine using the antibodies and conjugates of the invention for the detection of infections caused by *Pseudomonas aeruginosa*.

BACKGROUND OF THE INVENTION

Hospital-acquired infections (HAI) continue today to be one of the first causes of death in developing countries. It is estimated that each year in the European Union (EU) 4 million patients acquire a HAI and approximately 37000 of them die as a direct consequence of the infection. *Pseudomonas aeruginosa* is an opportunistic microorganism frequently isolated in intensive care units (ICU), present in pneumonias, cystic fibrosis (CF), bloodstream infections and some immunosuppressant diseases. The current lack of specific diagnostic tools is the cause of prescription of broad-spectrum antibiotics, which kill a large part of the bacteria due to the ignorance of the true microorganism responsible for the disease. The formation of biofilms is an important characteristic of *P. aeruginosa* which significantly contributes to antimicrobial resistance and the chronic nature of these infections (*Nature* 2000, 407 (6805), 762-764). According to the report of the European Centre for Disease Prevention and Control (ECDC), *P. aeruginosa* is resistant to penicillin, ceftazidime, fluoroquinolones, aminoglycosides and carbapenems, and a combined resistance is common in 15% of the isolations resistant to at least three classes of antibiotics, and 5% of the isolations resistant to all the antimicrobial classes under surveillance. An infection by *P. aeruginosa* involves many virulence factors, such as proteases, hemolysins, exotoxin A and secondary metabolites such as pyocyanin (1-methoxy-5-methylphenazine) and 1-hydroxyphenazine. It has been informed that pyocyanin is related to quorum sensing bacteria (*FEMS Microbiol Lett* 2009, 290, 1-9, *Molecular Microbiology* 2006, 61 (5), 1308-1321). Due to its zwitterionic nature, it may penetrate the cell membranes and generate reactive oxygen species in the intracellular redox cycle, producing extensive damage in human cells.

Currently, pathogen identification methods are based on the classic enrichment of cell culture followed by the identification by biochemical means. These methods are time consuming and the detectability achieved is often insufficient unless long periods of cell culture enrichment are used (minimum of 24 hours). These long diagnostic times are inacceptable in the case of a sepsis where the patient may go into shock in a period of 24-48 h. To improve the current detection methods, PCR methods have been introduced which amplify and sequence a specific DNA target of the microorganism. The DNA amplification methods give important knowledge about the bacteria genome; however, these techniques have considerable limitations related to the need to be performed by highly qualified personnel, the requirement of DNA extraction is a tedious process and requires purification stages to amplify the genetic material, and despite these efforts, there are large difficulties for putting these processes into practice as devices which may be suitable for execution in small local laboratories, avoiding the need to carrier the samples to centralized facilities. Alternatively, the immunochemical analysis methods, already applied in the clinical laboratories, have evolved towards sophisticated and efficient immunosensor devices capable of providing real-time responses in the presence of a particular target in combination with recent discoveries in the principles of nanobiotechnology and focussing the benefits so that the needs for the clinical diagnosis field can be satisfied.

With respect to *P. aeruginosa*, certain authors have selected the pyocyanin pigment as an objective for improving the surveillance of this pathogen, due to its specificity for this species. HPLC methods have been described for the quantification of pyocyanin and its metabolite 1-hydroxyphenazine in biological matrices (*Trends in Molecular Medicine* 2004, 10 (12), 599-6069, *European Journal of Biochemistry* 1986, 159 (2), 309-313); however, they are not suitable for clinical diagnosis since it requires extractions and purification processes which significantly increase and complicate the analysis time. More recently, a carbon fibre sensor has also been published for the detection of pyocyanin (*Bioelectrochemistry* 2010, 77 (2), 114-119), reaching concentrations as high as 130 µM in the detection of sputum samples from patients with CF. However, this method is not completely specific, since other reagent redox substances could generate a signal, due to lack of a specific receptor. In terms of the immunochemical methods, highly specific and sensitive and which in addition offer the possibility of different assay formats, they have not been used for the detection of infections caused by *Pseudomonas aeruginosa* based on the detection of pyocyanin and/or its metabolites.

Phenazine-type structures have been published, such as the compound 9-hydroxyphenazine-2-carboxylic acid (Chem.Pharm. Bulletin 1959, 7, 88), and derivatives of pyocyanin with possible use as anticancer agents whose synthesis describes intermediate compounds of phenazine type (U.S. Pat. No. 4,845,222) but the use thereof as a hapten has not been disclosed.

Therefore, there is a need in the state of the art to develop methodologies alternative to those described in the state of the art for the detection of infections caused by *Pseudomonas aeruginosa* in biological samples, in particular by immunochemical methods.

SUMMARY OF THE INVENTION

In a first aspect, the invention relates to a compound of general formula I:

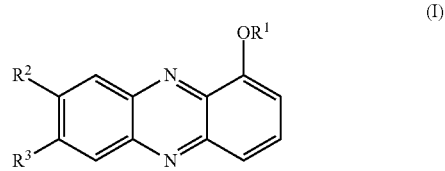

wherein
$R^1$ is selected from among H and $C_{1-4}$ alkyl;
$R^2$ is selected from among H and $(CH_2)_m$—$COR^4$:
$R^3$ is $(CH_2)_m$—$COR^4$ if $R^2$ is H, or $R^3$ is H if $R^2$ is $(CH_2)_m$—$COR^4$;
$R^4$ is selected from among H and $OR^5$;

$R^5$ is selected from among H and $C_{1-4}$ alkyl
m is a whole number selected from among 0 and 6;
with the condition that said compound is not

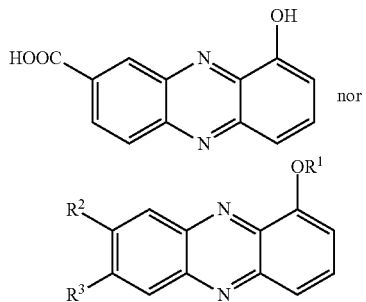 nor (I-a)

where
$R^1$ is selected from among H and $C_{1-2}$ alkyl, $R^2$ is $(CH_2)_{1-3}COOR^5$, $R^3$ is H and $R^5$ is selected from among H and $CH_3$ (I-b); or
$R^1$ is selected from among H and $C_{1-2}$ alkyl, $R^2$ is H, $R^3$ is $(CH_2)_{1-3}COOR^5$ and $R^5$ is selected from among H and $CH_3$ (I-c).

In a second aspect, the invention relates to the use of at least one compound of general formula I as hapten (hereinafter hapten of the invention):

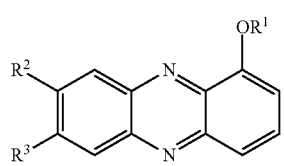

(I)

wherein
$R^1$ is selected from among H and $C_{1-4}$ alkyl;
$R^2$ is selected from among H and $(CH_2)_m$—$COR^4$:
$R^3$ is $(CH_2)_m$—$COR^4$ if $R^2$ is H, or $R^3$ is H if $R^2$ is $(CH_2)_m$—$COR^4$;
$R^4$ is selected from among H and $OR^5$;
$R^5$ is selected from among H and $C_{1-4}$ alkyl
m is a whole number selected from among 0 and 6;

In another aspect, the invention relates to a conjugate, also referred in the present description as conjugate of the invention, comprising at least one hapten of formula I (hapten of the invention) such as any of those defined above, and a second component selected from the group of:
(a) a carrier protein or a fragment thereof which gives antigenicity,
(b) a detectable labelling agent, and
(c) a polymer or a support.

In another aspect, the invention relates to a method for producing a conjugate according to the invention consisting of creating a covalent bond between the hapten of formula I and the protein, or between the hapten of formula I and the detectable labelling agent, either directly or through a binding group.

In even another aspect, the invention relates to the use of a conjugate according to the invention for producing antibodies.

In another aspect, the invention relates to an antibody obtained against at least one conjugate of the invention, or a polypeptide which has at least one fragment of the sequence of said antibody with capacity of binding to the antigen.

In another aspect, the invention relates to the use of the previous antibody in the detection and/or quantification of pyocyanin and/or 1-hydroxyphenazine for the detection of Pseudomonas aeruginosa in a sample of a subject.

In even another aspect, the invention relates to a method for the detection and/or quantification of pyocyanin and/or 1-hydroxyphenazine for the detection of Pseudomonas aeruginosa in a sample comprising the use of an antibody according to the invention or of a fragment thereof with capacity of binding to the antigen.

In a last aspect, the invention relates to a kit for the detection and/or quantification of pyocyanin and/or 1-hydroxyphenazine in a sample of a subject comprising at least one conjugate according to the invention and at least one anti-phenazine antibody.

DETAILED DESCRIPTION OF THE INVENTION

Figure 1:
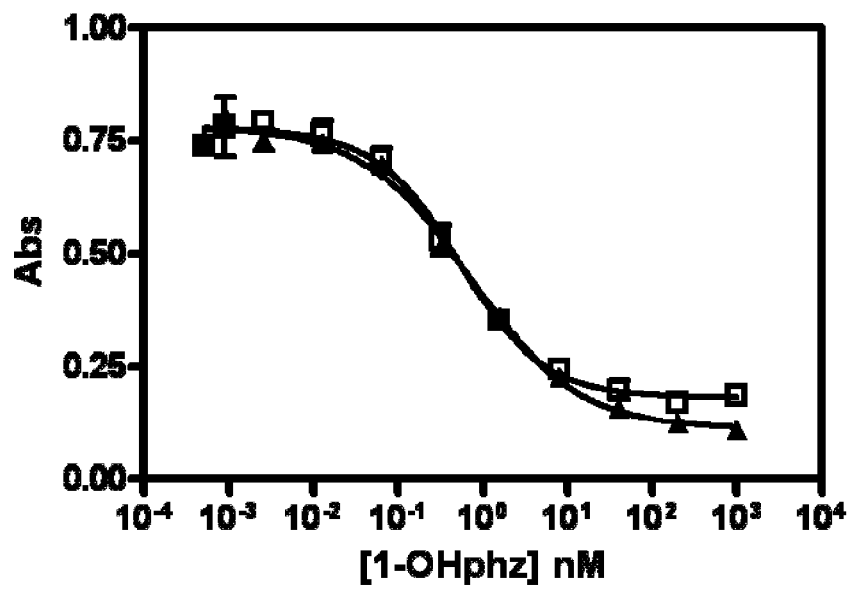
FIG. 1. Calibration curve of the ELISA As230/PC1-BSA (AE) used for the analysis of 1-hydroxyphenazine (1-OHphz) (top) and 1-hydroxyphenazine after the conversion of pyocyanin into this metabolite (bottom). Top: Calibration curve prepared in PBhST and sputum diluted 1/20 (Legend: □ PBhST; ▲ Sputum 1:20). Bottom: Calibration curve prepared in hydrolysis buffer and hydrolyzed sputum diluted 1/20. The data of the buffer curves correspond to a mean of N=3, where each measurement is made in triplicate, the data shown for the curves in sputum are the mean and standard deviation of at least two replicated wells (Legend: □ Hydrolysis buffer; ▲ Sputum 1:20 in 250 mM PBS). See table 1 to know the immunoassay parameters. The sputum is a mixture of sputa of 10 individuals not contaminated by P. aeruginosa.
Figure 1:
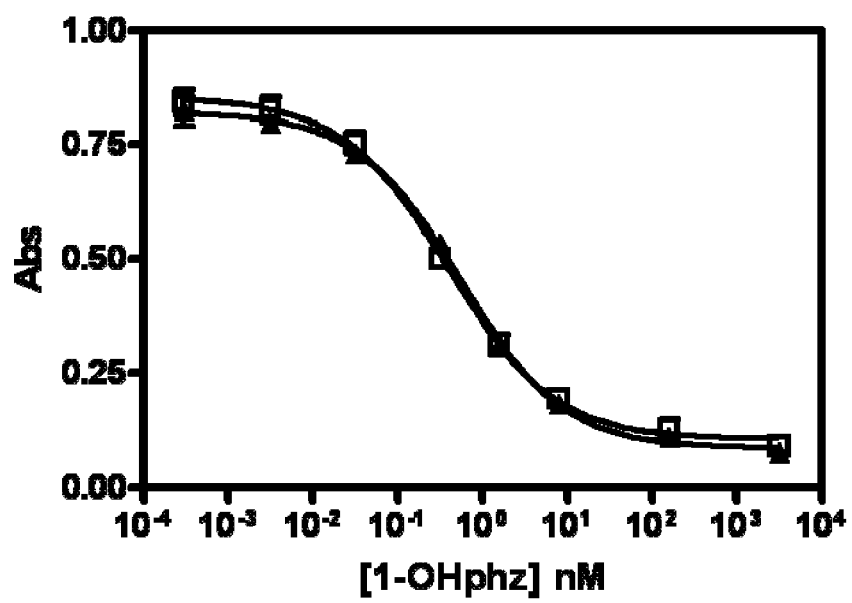

The authors of the present invention have designed haptens structurally related to pyocyanin, a toxin secreted by the Gram-negative bacteria Pseudomonas aeruginosa, and its derivatives, such as 1-hydroxyphenazine, for the production of specific antibodies against these compounds. In particular, with the antibodies produced, a diagnostic tool has been developed which allows the quantification of 1-hydroxyphenazine and/or pyocyanin in biological samples of patients who may have this bacteria.

The present invention has its key in the design and synthesis of immunization haptens, the structure whereof has allowed the production of specific antibodies. The inventors have determined the structures and synthesis of said haptens, hapten-protein bioconjugates, the immunochemical analysis process and its evaluation with samples of patients. The antibodies and the corresponding assay are valid for their use in any type of immunochemical analysis configuration such as, for example, ELISA-type formats, lateral-flow immunoassay (LFIA,) or of strip, Western-blot, immunoturbidimetry or immunosensors. They are also useful for the preparation of immunoaffinity extraction systems, whether, although not being limited to, immunoaffinity columns or particles biofunctionalized with the antibody, or any other type of support which allows the anchoring of the antibody for the later use of the biohydrid material for the extraction by specific interactions with the antibody.

Definitions

The term "antigen" makes reference to a molecule, such as a peptide, a carbohydrate, a glycolipid, a glycoprotein or a small molecule which is recognized and is bound to an antibody. The part of the antigen which is the target of the antibody bond corresponds to the antigenic determinant. In the context of the present invention, the antigen relates to a hapten according to the invention conjugated with a carrier protein, said conjugate being the one that is recognized and is bound to the specific antibodies obtained against the phenazine compounds of the invention.

In the context of the present invention, an "immunogen" is a conjugate according to the invention capable of triggering an immune response. The term "antiserum" relates to a serum obtained after the immunization of an animal with an immunogen. The antiserum comprises specific antibodies of said immunogen generated after the immune response produced in the animal.

The term "adjuvant" relates to a compound, natural or synthetic, which on being administered together with an immunogen, increases in non-specific form the intensity of the immune response generated against said immunogen. The adjuvants have four main modes of action: improving the capture and localization of antigens, extended antigen release, activation of macrophages and stimulation of B and T-cells. The most commonly used adjuvants are classified in six categories: mineral salts, oil emulsions, products of mycobacteria, saponins, synthetic products and cytokines. The adjuvants include, without being limited to, Freund's adjuvant, complete or incomplete, Titermax gold adjuvant, alum and bacterial LPS.

The term "antibody", as used here in the present invention, relates to immunoglobulin molecules and immunologically active portions of immunoglobulin molecules, i.e. molecules containing an antigen fixing site which specifically binds (immunoreacts) with an antigen, such as, for example, a protein. There are 5 isotypes or main classes of immunoglobulins: immunoglobulin M (IgM), immunoglobulin D (IgD), immunoglobulin G (IgG), immunoglobulin A (IgA) and immunoglobulin E (IgE). The term "antibody" comprises any type of known antibody such as, but not being limited to, for example, polyclonal antibodies or monoclonal antibodies, intact, or fragments thereof; and includes human, humanized and non-human origin antibodies. In the context of this invention, the term antibody relates to the immunoglobulin that the animal or a hybrid cell has synthesized specifically against the conjugated hapten of the invention.

"Monoclonal antibodies" are homogenous populations of identical antibodies, produced by a hybrid cell product of the fusion of a clone of B lymphocytes descendent of a single and unique stem cell and a tumour plasma cell, which are directed against a single site or antigenic determinant. "Polyclonal antibodies" include heterogeneous populations of antibodies, which are directed against different antigenic determinants.

The term "conjugate" relates in the present invention to the complex formed by the covalent bond of a hapten according to the invention and a second component which is selected from the group formed by a carrier protein or a fragment thereof which gives antigenicity, a detectable tag and a polymer or a support, in particular it relates to the hapten-carrier protein complex. Methods for producing hapten-carrier protein conjugates are known by a person skilled in the art.

The term "detectable tag" or "labelling agent" relates to a molecular tag which allows the detection, localization and/or identification of the molecule whereto it is bound, by processes and equipment suitable for the detection, either by spectroscopic, photochemical, biochemical, immunochemical or chemical means. Preferably, the detectable labelling agents are selected from an enzyme, a luminescent substance, a radioactive substance, a fluorophore substance, nanoparticles or mixtures thereof. By way of non-limiting illustration, examples of enzymes may be peroxidase, glycosidase, alkaline phosphatase, glucose-6-phosphate dehydrogenase, β-galactosidase, β-glucosidase, β-glucuronidase, luciferase, etc. Non-limiting examples of (chemi)luminescent substances are dioxetanes, acridines, phenanthridines, ruthenium, luminol, etc. Non-limiting examples of radioactive substances are sulfur, iodine, etc., specifically radioisotopes or radionuclides which may include, without limitation, $^3H$, $^{14}C$, $^{15}N$, $^{35}S$, $^{90}Y$, $^{99}Tc$, $^{111}In$, $^{125}I$, $^{131}I$. Non-limiting examples of fluorescent compounds may be fluorescein, rhodamine, lanthanide phosphors, FITC, etc. The detectable labelling agent may also be a nanoparticle and other types of particulated markers (latex, gold, quantum dots), metal complexes ($Tb^{3+}$, $Eu^{3+}$), enzymatic cofactors (FAD), etc.

"Phenazine" or "phenazine compound of the invention" relates in the present invention to a chemical compound which maintains the part of the chemical structure of two benzene rings bound together by an inner benzene ring, wherein the two carbon atoms have been replaced by nitrogen atoms which is segregated by *Pseudomonas aeruginosa* and which is responsible for their specific recognition by the antibodies of the invention. Preferably, the phenazines segregated by *Pseudomonas aeruginosa* are pyocyanin and/or 1-hydroxyphenazine.

The term "$C_{1-4}$ alkyl" relates in the present invention to a radical derived from a monovalent alkane (hydrocarbon), of linear or branched chain, containing from one to four carbon atoms and includes groups such as methyl, ethyl, propyl, isopropyl, butyl, isobutyl, sec-butyl or tert-butyl. Similarly, the term "$C_{1-2}$ alkyl" is used in this specification to refer to alkyl groups of 1 or 2 carbon atoms, such as methyl or ethyl groups.

The term "hapten", as used in the present invention, relates to a molecule of low molecular weight, which by itself is not capable of generating an immune response in an animal and needs to be bound to a carrier molecule to generate an immune response. Therefore, the hapten is a small molecule of non-immunogenic character with the capacity of inducing the formation of antibodies when it is bound to a carrier molecule, in particular a carrier protein. In the present invention, the hapten is a structural analog of the pyocyanin of formula I:

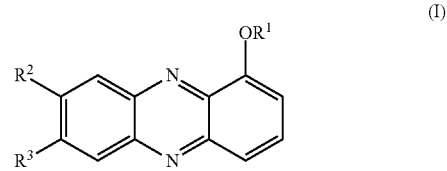

(I)

The term "carrier protein" or "transport protein" or "carrier", in the context of the present invention, relates to a protein or to a fragment thereof which, on being bound to a hapten, is responsible that said hapten, in an animal organism, turns into an immunogen with the capacity of inducing antibody formation. In said conjugate the hapten is responsible for inducing the desired specificity in the immune response, and the carrier molecule is responsible for giving antigenicity to the hapten, i.e. the capacity of behaving as an antigen. Proteins useful as carrier molecules for this invention are proteins with a molecular mass greater than 10 kDa, preferably greater than 15 kDa. Examples of carrier proteins according to the invention include, without being limited to, horseshoe crab hemocyanin (HCH), keyhole limpet hemocyanin (KLH), serum albumin of various species such as bovine serum albumin (BSA), rabbit serum albumin (RSA), horseradish peroxidase (HRP), ovalbumin (OVA), conalbumin (CONA), thyroglobulin and fibrinogen, and fragments of said proteins which give antigenicity. Preferred carrier proteins according to the invention are horseshoe crab hemocyanin (HCH) and bovine serum albumin (BSA).

The term "immunochemical technique of analysis" is an immunochemical method of analysis wherein an antibody is used which specifically binds to an antigen. The immunochemical technique of analysis is characterized by the use of specific binding properties of a particular antibody to isolate, direct and/or quantify the antigen. The immunochemical techniques comprise, without being limited to, immunoassays such as ELISA (Enzyme-Linked Immunosorbent Assay), LFIA (Lateral-flow immunoassay) Western-blot, RIA (radioimmunoassay), competitive EIA (enzyme immunoassay), DAS-ELISA (Double Antibody Sandwich-ELISA), immunocytochemical techniques and immunohistochemical techniques, techniques based on the use of biomarker, biosensor or microarray biochips, which include specific antibodies or assays based on colloidal precipitation in formats such as "dipsticks". Other immunochemical techniques include immunosensors whose transduction principle may be optical, electrochemical, piezoelectric, mass or thermometric. It also includes the immunosorbents or immunoaffinity extraction systems, which allow the selective extraction of an analyte within a complex mixture. These systems, usually of biohydrid materials, result from the stable union of the antibody to a solid support (polymer, inorganic material, metal particles, etc.), and which are used for the separation or extraction of the analyte from the rest of the matrix's components.

The term "detection method" relates to a method which allows establishing if a certain sample does or does not comprise 1-hydroxyphenazine and/or pyocyanin with a suitable sensitivity and specificity. The typical detection sensitivity ranges may be between approximately 20% and approximately 90% of the maximum signal.

The term "quantification method" relates to a method which allows establishing the concentration of 1-hydroxyphenazine and/or pyocyanin present in a sample. The typical quantification ranges may be between approximately 20% and approximately 80% of the maximum signal.

The term "sample", as used in the present invention, relates to a sample to be analysed by the method of the invention, susceptible of containing the phenazines of the invention, in particular pyocyanin and/or 1-hydroxyphenazine as markers of infections caused by *Pseudomonas aeruginosa*, which has been previously obtained from the subject under study (unless indicated otherwise). Illustrative, non-limiting examples of samples include both biological samples of tissues and body fluids, such as, for example, blood, serum, plasma, saliva, sputum, ear suppurations, bronchial washes, tissue exudates, etc. In a particular embodiment, said sample is sputum. In another particular embodiment, said sample is plasma. Furthermore, the sample may come, for example, from cell cultures, environmental samples such as water, soil or surface.

The term "pyocyanin", as used in the present invention, relates to a toxin secreted by the Gram-negative bacteria *Pseudomonas aeruginosa*. Pyocyanin, and its metabolites, in particular 1-hydroxyphenazine, may be used as marker of the infection of an organism with *Pseudomonas aeruginosa*.

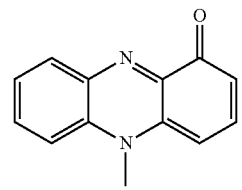

Pyocyanin

The expressions "specifically binds to" or "specifically immunoreactive with", in relation to an antibody, relate to a binding reaction which is determinant of the presence of an antigen or a determined immunogen in the presence of a heterogeneous population of proteins, saccharides and other biological products. Therefore, in established immunoassay conditions, the specific antibodies preferably bind to a particular antigen or immunogen and do not bind in significant quantity to other molecules present in the sample. The specific binding to an antigen or an immunogen in said conditions requires an antibody which may be selected for its specificity for a particular antigen or immunogen. A variety of immunoassay formats may be used to select antibodies especially immunoreactive with a particular antigen or immunogen. For example, solid-phase ELISA immunoassays are routinely used to select monoclonal antibodies specifically reactive with an antigen. See, Harlow and Lane (1988) Antibodies, A Laboratory Manual, Cold Spring Harbor Publications, New York, for a description of immunoassay formats and conditions which may be used to determine specific immunoreactivity.

The expressions "specifically (or selectively) binds to an antibody" or "specifically (or selectively) immunoreacts with", when it relates to a protein or peptide, in particular in the context of the present invention to a conjugate with immunogenic character according to the invention, relates to a binding reaction which is determinant of the presence of the conjugate, frequently in a heterogeneous population of proteins and other biological products. Therefore, in designated immunoassay conditions, the specific antibodies bind to a particular protein at least two times the background level and more typically more than 10 to 100 times the background level. The specific binding to an antibody in said conditions requires an antibody which is selected for its specificity for a particular protein. For example, the polyclonal antibodies made against the IgE protein, polymorphic variants, alleles, orthologs and conservatively modified variants, or splice variants, or parts thereof, may be selected to obtain only those polyclonal antibodies which are specifically immunoreactive with IgE proteins and not with other proteins. This selection may be achieved by taking away the antibodies which give cross-reaction with other molecules. A variety of immunoassay formats may be used to select antibodies specifically immunoreactive with a particular protein.

The term "support", as used in the present invention, relates to any solid material whereto the components of the invention, in particular the antibodies, the haptens or the bioconjugates of the invention, are physically bound, thus being immobilized. Any of a wide variety of solid supports may be used in the immunoassays of the present invention. The suitable materials for the solid support are synthetic such as polystyrene, polyvinyl chloride, polyamide or other synthetic polymers, natural polymers such as cellulose, and derivative natural polymers such as cellulose acetate or nitrocellulose, and glass, especially glass fibres. The support may take the form of spheres, sticks, tubes and microassay or microtiter plates. Structures similar to sheets such as strips of paper, small plates and membranes are also suitable. The surface of the supports may be permeable and impermeable for aqueous solutions. Additional inorganic solid supports suitable for their use in the present invention include, but are not limited to, silicon, crystal, quartz, ceramic, metals and their oxides, silica, silicates, silicides, nitrides, amorphous silicon carbide and any other material suitable for microfabrication or microlithography. Additional organic solid supports suitable for their use in the present invention include, without limitation, polymers such as polyimide, acrylate, polymethylmetacrylate, polystyrene or nitrocellulose.

In the present invention, the term "polymer" relates to a macromolecule formed by the binding of a finite quantity of smaller molecules called monomers, which give it a high molecular weight, in solid, liquid or gel, form, soluble or insoluble in organic or aqueous media. The term polymer includes oligomers and both homopolymers and copolymers, and may be selected from among natural and synthetic polymers. Examples of polymers useful in the present invention are, without being limited to, simple or modified dextran, polypyrrole, polyaniline, polylactic acid, polyethylene glycol or polylysine.

The term "subject", as used here, relates to all animals classified as mammals and includes, but is not limited to, domestic and farm animals, primates and human beings, for example, human beings, non-human primates, cows, horses, pigs, sheep, goats, dogs, cats or rodents. Preferably, the subject or patient is a man or women of any age or race.

Hapten of the Invention

In a first aspect, the invention relates to a compound of general formula I:

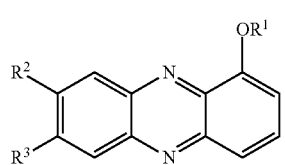

wherein
$R^1$ is selected from among H and $C_{1-4}$ alkyl;
$R^2$ is selected from among H and $(CH_2)_m$—$COR^4$;
$R^3$ is $(CH_2)_m$—$COR^4$ if $R^2$ is H, or $R^3$ is H if $R^2$ is $(CH_2)_m$—$COR^4$;
$R^4$ is selected from among H and $OR^5$;
$R^5$ is selected from among H and $C_{1-4}$ alkyl
m is a whole number selected from among 0 and 6;
with the condition that said compound is not

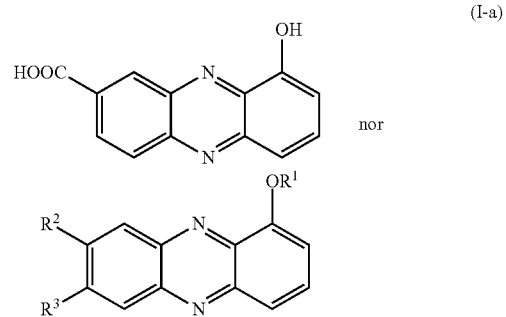

wherein
$R^1$ is selected from among H and $C_{1-2}$ alkyl, $R^2$ is $(CH_2)_{1-3}COOR^5$, $R^3$ is H and $R^5$ is selected from among H and $CH_3$ (I-b); or
$R^1$ is selected from among H and $C_{1-2}$ alkyl, $R^2$ is H, $R^3$ is $(CH_2)_{1-3}COOR^5$
and $R^5$ is selected from among H and $CH_3$ (I-c).

In a second aspect, the invention relates to the use of at least one compound of general formula I:

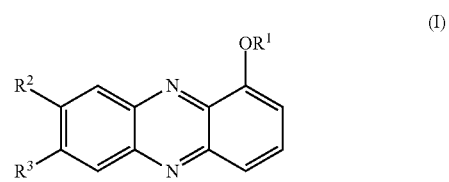

wherein
$R^1$ is selected from among H and $C_{1-4}$ alkyl;
$R^2$ is selected from among H and $(CH_2)_m$—$COR^4$;
$R^3$ is $(CH_2)_m$—$COR^4$ if $R^2$ is H, or $R^3$ is H if $R^2$ is $(CH_2)_m$—$COR^4$;
$R^4$ is selected from among H and $OR^5$;
$R^5$ is selected from among H and $C_{1-4}$ alkyl
m is a whole number selected from among 0 and 6;
or of a combination thereof, as hapten (hereinafter, hapten of the invention).

In a particular embodiment, at least one compound of formula I is used as hapten, wherein:
$R^1$ is selected from among H and $C_{1-4}$ alkyl,
$R^2$ is selected from among H and $(CH_2)_m$—$COR^4$,
$R^3$ is $(CH_2)_m$—$COR^4$ if $R^2$ is H, or $R^3$ is H if $R^3$ is $(CH_2)_m$—$COR^4$,
$R^4$ is selected from among H and $OR^5$,
$R^5$ is selected from among H and $C_{1-4}$ alkyl,
m is a whole number selected from among 0 and 6,
with the condition that said compound is not a compound of general formula I of the following:
I-a. wherein $R^1$ is H, $R^2$ is COOH and $R^3$ is H; or
I-b. wherein $R^1$ is selected from among H and $C_{1-2}$ alkyl, $R^2$ is selected from among $(CH_2)_{1-3}$—COOH and $(CH_2)_{1-3}$—$COOCH_3$ and $R^3$ is H; or
I-c. wherein $R^1$ is selected from among H and $C_{1-2}$ alkyl, $R^2$ is H and $R^3$ is selected from among $(CH_2)_{1-3}$—COOH and $(CH_2)_{1-3}$—$COOCH_3$.

And in a more preferred embodiment of the above, in addition to said compound of formula I, it comprises at least one second compound of formula I wherein:
$R^1$ is selected from among H and $C_{1-4}$ alkyl,
$R^2$ is selected from among H and $(CH_2)_m$—$COR^4$, $R^3$ is $(CH_2)_m$—$COR^4$ if $R^2$ is H, or $R^3$ is H if $R^3$ is $(CH_2)_m$—$COR^4$,
$R^4$ is selected from among H and $OR^5$,
$R^5$ is selected from among H and $C_{1-4}$ alkyl,
m is a whole number selected from among 0 and 6, In a particular embodiment of any of the previous, in the compound used as hapten, $R^1$ is H.

In another particular embodiment of any of the previous, in the compound used as hapten, $R^2$ is H and $R^3$ is COOH.

In another particular embodiment of any of the previous, in the compound used as hapten $R^2$ is COOH and $R^3$ is H.

In a preferred embodiment, this hapten is 9-hydroxyphenazine-2-carboxylic acid.

In another preferred embodiment this hapten is 6-hydroxyphenazine-2-carboxylic acid.

In a more preferred embodiment of any of the previous, it is a mixture of haptens. In an even more preferred embodiment, the mixture of haptens comprises 9-hydroxyphenazine-2-carboxylic acid and 6-hydroxyphenazine-2-carboxylic acid. Hereinafter, this mixture of haptens is called "mixture of PC1 haptens"

Method of Synthesis of the Hapten of the Invention

The haptens of general formula I may be prepared following different methods known by a person skilled in the field of organic synthesis, in particular it may be synthesized from the condensation of an ortho-quinone with a phenylenediamine, by the following synthetic process:

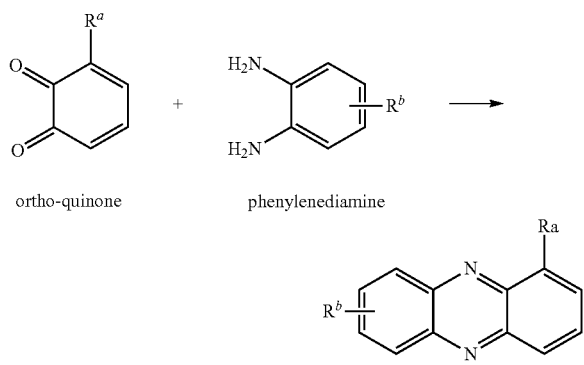

where $R^a$ is selected from the group consisting of: —OH, —O—$C_{1-4}$alkyl; $R^b$ is —$(CH_2)_m COR^4$, where m is a whole number between 0 and 6, $R^4$ is selected from among —H and —$OR^5$, and where $R^5$ is selected from among —H and —$C_{1-4}$alkyl. In a preferred embodiment, the synthesis of the mixture of PC1 haptens, takes place following the following scheme:

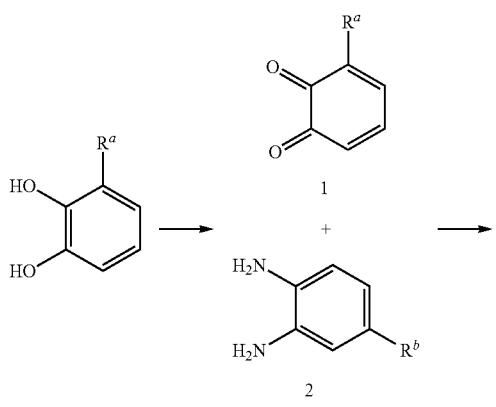

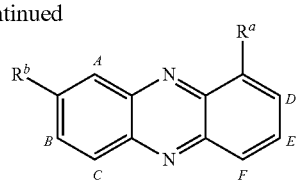

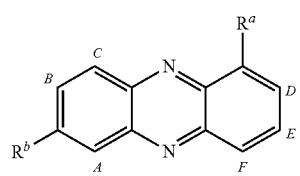

In a first stage, a condensation occurs of 3,4-diaminobenzoate 2 with benzoquinone 1 to obtain the corresponding phenazine derivatives. Benzoquinone 1 may be obtained by different methods, such as, for example, by oxidation with o-chloranil of 3-methoxycatechol. The condensation of 1 and 2 produce alkyl alkoxyphenazinylcarboxylate 3, as a mixture of position isomers. In a later stage, a dealkylation occurs of the aromatic ether, using, for example, boron tribromide and obtaining the mixture of compounds 4. Then, the alkyl ester is hydrolyzed in alkaline medium, to obtain the mixture of PC1 haptens (5).

In a particular embodiment of the invention, the compounds from which the hapten or the mixture of haptens of formula I of the invention is derived are selected from the group formed by pyocyanin and 1-hydroxyphenazine.

In a preferred embodiment, the synthesis of the PC1 hapten, i.e. the mixture of 9-hydroxyphenazine-2-carboxylic acid and 6-hydroxyphenazine-2-carboxylic acid, conserves the phenazine rings as epitopes and, according to the invention, and as shall be explained below, it is used in the generation of specific antibodies of 1-hydroxyphenazine.

Conjugate of the Invention

The authors of the present invention have obtained conjugates of the haptens of the invention with carrier proteins, with labelling agents or with polymers or inorganic supports.

Therefore, another aspect of the invention is a conjugate comprising at least one hapten of formula I,

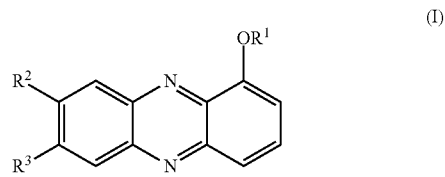

wherein:
$R^1$ is selected from among H and $C_{1-4}$ alkyl,
$R^2$ is selected from among H and $(CH_2)_m$—$COR^4$,
$R^3$ is $(CH_2)_m$—$COR^4$ if $R^2$ is H, or $R^3$ is H if $R^3$ is $(CH_2)_m$—$COR^4$,
$R^4$ is selected from among H and $OR^5$,
$R^5$ is selected from among H and $C_{1-4}$ alkyl, and
m is a whole number selected from among 0 and 6;
or a combination thereof, and a second component selected from the group of:
(a) a carrier protein or a fragment thereof which gives antigenicity,
(b) a labelling agent, and
(c) a polymer or a support.

In a particular embodiment, it is a conjugate comprising at least one hapten of formula I,

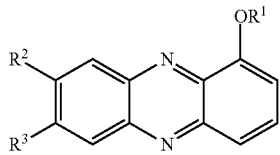
(I)

wherein:

R¹ is selected from among H and $C_{1-4}$ alkyl,

R² is selected from among H and $(CH_2)_m$—COR⁴,

R³ is $(CH_2)_m$—COR⁴ if R² is H, or R³ is H if R³ is $(CH_2)_m$—COR⁴,

R⁴ is selected from among H and OR⁵,

R⁵ is selected from among H and $C_{1-4}$ alkyl, and m is a whole number selected from among 0 and 6;

with the condition that said compound is not a compound of general formula I of the following:

I-a. wherein R¹ is H, R² is COOH and R³ is H; or

I-b. wherein R¹ is selected from among H and $C_{1-2}$ alkyl, R² is selected from among $(CH_2)_{1-3}$—COOH and $(CH_2)_{1-3}$—COOCH₃ and R³ is H; or I-c. wherein R¹ is selected from among H and $C_{1-2}$ alkyl, R² is H and R³ is selected from among $(CH_2)_{1-3}$—COOH and $(CH_2)_{1-3}$—COOCH₃, and a second component selected from the group consisting of:

a. a carrier protein, or a fragment thereof, which gives antigenicity, b. a detectable labelling agent, and c. a polymer or a support.

And in a particular more preferred embodiment of the above, in addition to said hapten of general formula I, it comprises a second hapten of formula I,

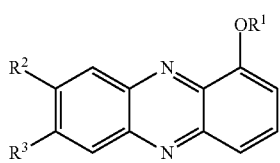
(I)

wherein:

R¹ is selected from among H and $C_{1-4}$ alkyl,

R² is selected from among H and $(CH_2)_m$—COR⁴,

R³ is $(CH_2)_m$—COR⁴ if R² is H, or R³ is H if R³ is $(CH_2)_m$—COR⁴,

R⁴ is selected from among H and OR⁵,

R⁵ is selected from among H and $C_{1-4}$ alkyl, and m is a whole number selected from among 0 and 6.

In a particular embodiment, in the conjugate such as any of those defined above in this aspect of the invention, the hapten of formula I comprises a mixture of 9-hydroxyphenazine-2-carboxylic acid (II) and 6-hydroxyphenazine-2-carboxylic acid (III).

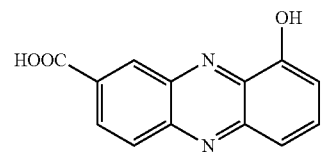
(II)

9-hydroxyphenazine-2-carboxylic acid

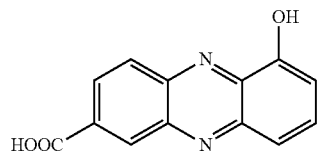
(III)

6-hydroxyphenazine-2-carboxylic acid

In a particular embodiment of any of the previous, the second component is a carrier protein, or a fragment thereof, which gives antigenicity, or a polymer or a support.

In another particular embodiment of any of the previous, the conjugate according to the invention has immunogenic character, i.e. it induces the formation of antibodies. Thus, the conjugate of the invention comprises a hapten as described above and a carrier protein, wherein said carrier protein is responsible for the immunogenic character of the conjugate of the invention. It is known by the person skilled in the art that the intensity of the response of a subject to an immunogen is given by factors such as the size of the immunogen, its chemical characteristics, and its difference with respect to the actual proteins of the subject in which the immunization takes place. In general, immunogens have a molecular weight greater than 5 kDa, and their phylogenetic origin is distant with respect to those of the subject wherein the immunization occurs.

The immunization process against the conjugate of the invention requires that said conjugate is highly purified. The response to an immunogen increases as repeated exposure occurs to said immunogen, or the immunogen is administered in combination with a suitable adjuvant.

The carrier protein of the conjugate according to the invention is a protein which, conjugated to the hapten according to the invention, confers immunogenicity to said hapten. Methods to determine that a conjugate is immunogenic are known by persons skilled in the art, and comprise, without being limited to, determination of the generation of specific antibodies to said immunogen by techniques such as ELISA, western blotting, etc.

Preferred carrier proteins according to the invention are horseshoe crab hemocyanin (HCH), bovine serum albumin (BSA), horseradish peroxidase (HRP), ovalbumin (OVA) and conalbumin (CONA). In a particular embodiment of the invention, the carrier protein that forms part of the conjugate of the invention is selected from the group formed by BSA and HCH.

The present invention also contemplates variants of carrier proteins or fragments thereof, with a similarity of at least 80%, 85%, 90%, 95% or 99% with respect to the carrier protein.

In a particular embodiment, the hapten according to the invention may be bound to a labelling agent, by way of marker for its detection, as previously defined in the present description. In an alternative particular embodiment, the hapten may be bound to a polymer or a support, in particular to an inorganic polymer or support, as defined in the scope of the present invention.

Method for Producing the Conjugates of the Invention

Another aspect of the invention is a method for producing a conjugate according to the invention consisting of subjecting the hapten and the second component of the conjugate to a conjugation method.

In the conjugates of the invention between a hapten and a protein, the proteins are bonded to the hapten covalently by means of the amino acids accessible on their surface, preferably those amino acids with nucleophile-type side chains. The reactive amino acid of the proteins is selected from the list comprising, but without being limited to, cysteine, serine, tyrosine and lysine; it is preferably lysine. The processes to achieve the conjugation of haptens to other carrier molecules depend on the functional group present in the hapten molecule in question. It must also consider the stability and solubility of the hapten. Therefore, given the large variety of haptens that exist, there is no common conjugation method.

In an embodiment of the present invention, the hapten of formula I of the invention is conjugated to the carrier protein through the $R^2$ or $R^3$ group of said hapten, when $R^2$ or $R^3$ is other than H.

When the $R^2$ or $R^3$ group of the hapten is a carboxylic acid (—COOH), it is possible to use for the conjugation, among others, the mixed anhydride method, the carbodiimide method (CDI) or the N-hydroxysuccinimide ester method (NHS) (this latter also known as active ester method).

When the $R^2$ or $R^3$ group of the hapten is an aldehyde (CHO), this may be transformed into a carboxyl group by the formation of O-(carboxymethyl)oximes. The reaction is performed by treating the hapten with O-(carboxymethyl) hydroxylamine. The reaction of the carboxylic acid formed with the protein is continued by one of the aforementioned methods. The haptens which have formyl groups may also be directly coupled through the formation of Schiff bases, which are transformed to amines by reduction with sodium borohydride.

All these conjugation methods are well known in the state of the art and are described in summarized form in Guerra et al. 2003 (Guerra M., Morris H. 2003. Revista Cubana de Quimica, vol. XV, no. 2) and more at length in Bartos et al. 1998 (Bartos E., Practice and Theory of Enzyme Immunoassays, Barcelona, 1988, pages 279-296). Said methods are shown here by way of illustration and not in a limiting sense, since other conjugation methods known by persons skilled in the art may be used.

In a particular embodiment, when the hapten of formula I is the mixture of PC1 haptens, the process for producing the conjugate of these haptens with the carrier protein comprises the activation of the carboxylic acid of the hapten and the reaction of the hapten activated with the carrier protein.

In a particular embodiment, the activation of the carboxylic acid ($R^2$ or $R^3$) is carried out by the mixed anhydride method, the carbodiimide method (CDI) or the method of the N-hydroxysuccinimide ester (NHS).

In a particular embodiment, when the hapten of formula I is the mixture of PC1 haptens, it is bound to the HCH protein or a fragment thereof by the mixed anhydride conjugation method.

In a particular embodiment, when the hapten of formula I is the mixture of PC1 haptens, it is bound to the BSA protein or a fragment thereof by the mixed anhydride conjugation method or by the N-hydroxysuccinimide ester conjugation method.

In a particular embodiment of the conjugate of the invention, the hapten and the carrier protein are bound by a cross-linking agent.

For the protein cross-linking, the functional protein groups whereto to the cross-linking agents are targeted comprise amino groups, ε-amino groups of lysine, α-amino terminal groups, cysteine sulfhydryl groups (—SH or thiol groups), carbohydrate groups (in the case of glycoproteins) and carboxyl groups.

Cross-linking agents of proteins through amino groups, lysine ε-amino and terminal α-amino groups include, but without being limited to imidoesters and N-hydroxysuccinimide esters (NHS-esters).

Cross-linking agents of proteins through sulfhydryl groups include, without being limited to, maleimides, haloacetyls (such as iodoacetyl) and pyridyl disulfide (pyridyl-dithiols).

Cross-linking agents of proteins through carbonyl groups (such as aldehydes or ketones) by oxidative treatment of the glycoprotein carbohydrates include, without being limited to, reagents comprising hydrazides (—NH—NH$_2$—).

Cross-linking agents of proteins through carboxyl groups include, without being limited to, carbodiimides.

As persons skilled in the at understand, the choice of the suitable cross-linking agent for producing conjugates with immunogenic character depend on the functional groups present in the hapten and the capacity of the hapten-carrier protein to act as immunogen. Since the carrier proteins typically comprise several carboxyl groups and accessible primary aminos, a cross-linking agent typical for the hapten-carrier protein conjugation is carbodiimide, such as EDC.

All these conjugation methods are also useful for the synthesis of conjugates between a hapten and a labelling agent. The methods used for the conjugation between a hapten and a labelling agent are known in the state of the art. As persons skilled in the art will appreciate, to carry out this reaction, it is necessary that the labelling agent has a free functional group, preferably a carboxyl, aldehyde, halogen, sulfhydryl of amino functional group.

The conjugation between a hapten of formula I and a polymer or a support may be performed by using the same proteins as for the conjugation to proteins such as those that have been defined here, whether they directly have free functional groups or by a modification thereof which introduces a reactive functional group. Classically, for the inorganic supports, this has been performed for a silicon oxide and of other metals by heterobifunctional silanes or by functionalized thiols (for noble metal surfaces). Whilst for the polymers it directly uses those that have active functional groups from their base formulation.

Antibody that Recognizes the Conjugate of the Invention

In another aspect, the invention relates to the use of a conjugate comprising a hapten of the invention of general formula I and a carrier protein which gives antigenicity for producing antibodies.

The authors of the present invention have obtained, by immunization of animals with the conjugates of the invention, antiserums comprising specific polyclonal antibodies of said conjugates. This shows that the conjugate of the invention, of immunogenic character, may be used to generate an immune response, wherein specific antibodies are generated to said immunogenic conjugate. On the other hand, the authors of the present invention have determined that said antibodies generated specifically to the conjugate of the invention are capable of recognizing and specifically binding to phenazine derivatives, in particular 1-hydroxyphenazine.

Therefore, in another aspect, the invention relates to an antibody (antibody of the invention) that specifically recognizes the conjugate of the invention. Since the conjugate of the invention comprises a hapten derived from a phenazine, the antibody of the invention also specifically recognizes phenazine-type agents from which the hapten of the conjugate is derived.

Likewise, the invention relates to an antiserum comprising the antibody which recognizes and specifically binds the conjugate of the invention. Additionally, the invention relates to the use of the antibody or of the antiserum comprising said antibody in the detection and/or quantification of 1-hydroxyphenazine and/or pyocyanin in a sample for the detection of infections caused by *Pseudomonas aeruginosa*.

The antibody does not directly recognize pyocyanin. The quantification of pyocyanin present in a sample is performed directly after a conversion reaction of pyocyanin into 1-hydroxyphenazine by means of suitable chemical or biological agents and known by an average person skilled in the art, such as a treatment in base medium, such as for example NaOH, or enzyme treatment.

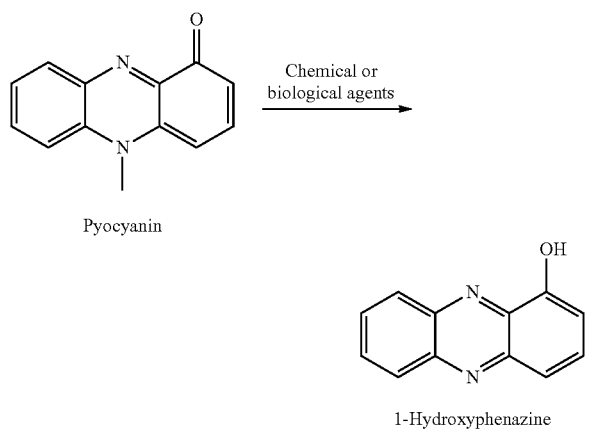

For the generation of antibodies, the immunogenic conjugate may be administered forming part of an immunogenic composition which may further comprise a pharmaceutically acceptable support. Said support may increase the immunogenicity of the conjugate or induce greater titers of antibodies. Useful supports include polymeric, which may be natural (e.g. polysaccharides, polypeptides or proteins of bacteria or virus), semisynthetic or synthetic materials containing one or more functional groups whereto a reactive group may be bound. Bacterial products and viral proteins may also be used (e.g. surface antigen and central antigen of the hepatitis B virus), as well as proteins of superior organisms such as Californian limpet hemocyanin, horseshoe crab hemocyanin, edestin, mammal serum albumins and mammal immunoglobulins. Additional bacterial products for use as supports include bacterial wall proteins (e.g. cell walls and lipopolysaccharide (LPS) of streptococcus and staphylococcus).

The immunogenic composition comprising the conjugate of the invention for the generation of antibodies may be administered by any means known by persons skilled in the art, such as by intramuscular, subcutaneous or intravenous injection and oral, nasal or anal administration. See, Banga A, "Parenteral Controlled Delivery of Therapeutic Peptides and Proteins", in Therapeutic Peptides and Proteins (Technomic Publishing Co., Inc., Lancaster, Pa., USA, 1995). It has been shown that a particular support based on a synthetic polymer acts as adjuvant to increase immune response, in addition to providing a controlled release. Aluminium salts may also be used as adjuvants to produce an immune response.

The antibody of the invention includes, without being limited to, polyclonal antibodies, monoclonal antibodies, single chain Fab and Fv fragments (scFv) thereof, bispecific antibodies, heteroconjugates, human and humanized antibodies. Said antibodies may be produced in a variety of modes, including hybridoma cultures, recombinant expression in mammal or bacteria cell cultures and recombinant expression in genetically modified animals. Antibodies may also be produced by selecting a sequence from a library of sequences expressed in presentation systems such as filamentous phages, bacteria, yeasts or ribosomes. There is an abundant guidance in the bibliography to select a particular production methodology, e.g. Chadd and Chamow, Curr. Opin. Biotechnol., 12:188-194 (2001). The choice of the manufacturing methodology depends on several factors that include the desired antibody structure, the ease of culture and purification, and the costs. Many different antibody structures may be generated using conventional expression technology, including full length antibodies, fragments of antibody, such as Fab and Fv fragments, and chimeric antibodies comprising components of different species. Fragments of small-sized antibody, such as Fab and Fv fragments, which do not have effector functions and which have limited pharmacogenic activity may be generated in a system of bacterial expression. Single-chain Fv fragments show low immunogenicity and are rapidly eliminated from the blood.

In a preferred embodiment, the antibodies are polyclonal antibodies. To produce polyclonal antibodies against a hapten of formula I, a non-human animal is immunized with a conjugate of the invention comprising said hapten and a carrier molecule which gives antigenicity according to methods known by a person skilled in the art. Once an acceptable titer of antibodies has been obtained, the animal is exsanguinated and the antiserum is collected containing the serum antibodies formed by said animal.

In another embodiment, the antibodies are monoclonal antibodies. The process for producing the monoclonal antibodies of the invention may be performed according to conventional methods, known in the state of the art. Basically, the method consists of immunizing an animal with a conjugate according to the invention comprising a hapten of formula (I) and a carrier molecule which gives immunogenicity, and later extracting cells from the spleen of the immunized animal, which are fused with myeloma cells in the presence of an infusion inductor, such as PEG-1500 by standard processes (Harlow D and Lane D. Antibodies: a laboratory manual. 1988. Cold Spring Harbor Laboratory Press, Cold Spring Harbor. N.Y.). The hybridomas are selected and subcloned by dilution. The suitable clones for their expansion are constituted in a hybridoma cell line. Then, said hybridoma cell line is cultured in a suitable culture medium so that the hybridoma cells produce antibodies and secrete them into the medium, and the supernatant is later collected from the culture medium containing the monoclonal antibodies produced. Optionally, said antibodies may be purified by conventional means, such as affinity chromatography, A-Sepharose protein, chromatography with hydroxyapatite, electrophoresis in gel or dialysis. Therefore, in an embodiment of the invention, the production of antibodies comprises the administration of a conjugate according to the invention and the collection of tissue cells of said animal capable of producing said antibodies.

Persons skilled in the art shall understand that the sequences of amino acids of the antibodies of the invention may include one or more substitutions of amino acids so that, although the primary sequence of the polypeptide is altered, the capacity is maintained of the antibody binding to the conjugate of the invention. Said substitution may be a conservative substitution and, in general, it is applied to indicate that the substitution of one amino acid for another amino acid with similar properties (for example, the substitution of glutamic acid (charged amino acid) by aspartic acid would be a conservative substitution of amino acids).

It also contemplates that the antibody of the invention may be marked with a detectable tag or labelling agent which allows its localization and/or identification, by spectroscopic, photochemical, biochemical or chemical means. Thus, in a particular embodiment, the antibody of the invention comprises a labelling agent.

Thus, in a particular embodiment, the antibody of the invention is modified covalently so that its later detection is possible. In principle, the invention contemplates the use of any marker provided that the covalent conjugation to the antibody is possible and that it allows the later detection of said antibody. Thus, the invention contemplates the possibility of modifying the antibody with a radioisotope of the type of $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$ or $^{213}B$. The labelling with radioisotopes is typically carried out by the use of chelating ligands which are capable of complexing metal ions such as DOTA, DOTP, DOTMA, DTPA and TETA (Macrocyclics, Dallas, Tex.).

In an alternative particular embodiment, the antibody of the invention is marked with a fluorescent group. The fluorescent group can be bound to the side chains of the amino acids directly or through a connector group. Methods for conjugating fluorescent reagents to polypeptides are well known in the state of the art and have been described, for example, in Haugland, 2003, Molecular Probes Handbook of Fluorescent Probes and Research Chemicals, Suitable reagents for the labelling of polypeptides, such as antibodies, with fluorescent groups include chemical groups which show capacity to react with the different groups which appear in the side chains of the proteins, including amino groups and thiol groups. Thus, chemical groups which may be used to modify the antibodies according to the present invention include, without limitation, maleimide, haloacetyl, succinimidyl ester iodoacetamide (for example, NHS, N-hydroxysuccinimide), isothiocyanate, sulfonyl chloride, 2,6-dichlorotriazinyl, pentafluorophenyl ester, phosphoramidite and similar. An example of suitable reactive functional group is N-hydroxysuccinimide ester (NHS) of a detectable group modified with a carboxyl group. Typically, the carboxyl group which modifies the fluorescent compound is activated by placing in contact said compound with a carbodiimide reagent (for example, dicyclohexylcarbodiimide, diisopropylcarbodiimide, or a uronium reagent such as TSTU (O—(N-Succinimidyl)-N,N,N',N'-tetramethyluronium tetrafluoroborate), HBTU ((O-benzotriazole1-yl)-N,N,N',N'-tetramethyluronium hexafluorophosphate), or HATU (O-(7-azabenzotriazole1-yl)-N,N,N',N'-tetramethyluronium hexafluorophosphate), an activator of type 1-hydroxybenzotriazole (HOBt) and N-hydroxysuccinimide to give rise to the NHS ester of the marker.

Suitable fluorescent compounds for their use in the present invention include, without limitation, ethidium bromide, SYBR Green, fluorescein isothiocyanate (FITC), tetramethyl rhodamine isothiol (TRIT), 5-carboxyfluorescein, 6-carboxyfluorescein, fluorescein, HEX (6-carboxy-2',4,4',5',7,7'-hexachlorofluorescein), Oregon Green 488, Oregon Green 500, Oregon Green 514, Joe (6-carboxy-4',5'-dichloro-2',7'-dimethoxyfluorescein), 5-carboxy-2',4',5',7'-tetrachlorofluorescein, 5-carboxyrhodamine, rhodamine, tetramethylrhodamine (Tamra), Rox (carboxy-X-rhodamine), R6G (rhodamine 6G), phthalocyanines, azomethines, cyanins (Cy2, Cy3 and Cy5), Texas Red, Princeston Red, BODIPY FL-Br2, BODIPY 530/550, BODIPY TMR, BODIPY 558/568, BODIPY 564/570, BODIPY 576/589, BODIPY 581/591, BODIPY TR, BODIPY 630/650, BODIPY 650/665, DABCYL, Eosin, Erythrsosine, ethidium bromide, green fluorescent protein (GFP) and their analogs, inorganic fluorescent markers based on semiconductor nanocrystals (Quantum dot), fluorescent markers based on lanthanides such as Eu3+ and Sm3+ and similar.

In an alternative particular embodiment, the antibodies are marked by conjugation with a first member of a bonding pair. In a preferred form, said covalent modification is a biotinylation. The term "biotinylation", as used in the present invention, relates to the covalent bond of biotin to a molecule (typically a protein). The biotinylation is carried out using reagents capable of conjugating biotin to the side chain of the proteins, wherein said conjugation fundamentally takes place in the primary amino groups and in the thiol groups which appear in the side chains of the proteins. Suitable reagents for the biotinylation of amino groups include molecules containing biotin and a group capable of reacting with amino groups such as succinimide esters, pentafluorophenyl esters of alkyl halides, with the biotin group and the reagent group being separated by a spacer of any length (for example, from 8-40 A in length). Some examples of these biotinylation agents include NHS-biotin agents (containing an ester bond of five carbon atoms between the biotin and the NHS group), sulfo-NHS-biotin, NHS-LC-biotin, sulfo-NHS-LC-Biotin, NHS-LC-LC-biotin, sulfo-NHS-LC-LC-biotin, sulfo-NHS-SS-biotin, NHS-PEO4-biotin, PFP-biotin, TFP-PEO-biotin and similar, wherein "NHS" indicates a N-hydroxysuccinimide group, "LC" relates to an amide-type bond of 6 carbon atoms located between the NHS group and biotin, "PEO" relates to an ethylene oxide group, wherein the subindex indicates the number of PEO units, "PFP" relates to a pentafluorophenyl group, "TFP" relates to a tetrafluorophenyl group, "sulfo" relates to a sulfonate group (SO3" Na+) and "SS" relates to a disulfide group. Examples of reactive biotinylation agents with thiol groups include molecules comprising biotin and a group of maleimide or alkyl halide type, separated by a spacer of any length. Examples of biotinylation reagents include maleimide-PEG-biotin, biotin-BMCC (containing a N-terminal maleimide group and a cyclohexyl group, 2 amide bonds and 9 binding carbon atoms), PEO-iodoacetyl biotin, iodoacetyl-LC-biotin, biotin-HPDP (containing a pyridyl disulphide group) and similar.

Use of the Antibody of the Invention

The antibody of the invention may be used in the determination and/or quantification of phenazines generated when a subject suffers an infection from *Pseudomonas aeruginosa*, in particular pyocyanin and/or 1-hydroxyphenazine and its derivatives in a sample of a subject.

The use of the antibody of the invention may be carried out in any type of immunochemical technique of analysis aimed at the detection, determination and/or quantification, or selective extraction of phenazines produced by *Pseudomonas aeruginosa*. Said immunochemical techniques of analysis comprise, without being limited to, ELISA, immunosorbents, immunoaffinity chromatography, strip or lateral-flow immunoassay, immunosensors, immunoprecipitation, Western blot, dot-blot, radioimmunoassay, immunofluorescence, immunohistochemistry and flow cytometry.

Therefore, in another aspect, the invention relates to the use of an antibody (use of the antibody of the invention) that specifically recognizes the conjugate of the invention in the detection and/or quantification of pyocyanin and/or 1-hydroxyphenazine in a sample obtained previously from a subject.

In a preferred embodiment, the sample of the subject is a sample of blood, urine or sputum. In an even more preferred embodiment, the sample wherein infections caused by *Pseudomonas aeruginosa* are detected, through the determination of the presence of phenazines, is a sputum sample.

Method for the Detection and/or Quantification of Pyocyanin and/or 1-Hydroxyphenazine The inventors have developed a method which allows detecting and/or quantifying the phenazines of the invention, in particular, 1-hydroxyphenazine and/or pyocyanin, in any type of sample by the use of the antibodies and conjugates of the invention.

Therefore, another aspect the invention relates to an in vitro method for the detection and/or quantification of 1-hydroxyphenazine and/or pyocyanin in a sample comprising the use of an antibody according to the invention or of a fragment thereof with capacity of binding to the antigen or an antiserum comprising the previous antibody. In the previous method, said use of the antibody comprises at least the following stages:

placing in contact the sample to be analysed with the antibody of the invention during the necessary time for their binding (incubation), identifying the formation of immunocomplexes formed with said antibody and/or measuring the quantity of said immunocomplexes.

Optionally, when the method of the invention comprises the detection and/or quantification of pyocyanin, it also comprises a previous treatment stage of the sample consisting of the conversion of pyocyanin in 1-hydroxyphenazine by means of suitable chemical or biological agents and known by an average person skilled in the art, such as treatment in base medium such as, for example, NaOH, or enzymatic treatment.

Additionally, said method, in any of its previous variants, may also require a conjugate according to the invention. In a particular embodiment, in addition to the antibody of the invention it uses a conjugate comprising a hapten of formula I and a second component which may be a carrier protein that gives antigenicity or a detectable labelling agent.

The method of the invention makes it possible not only to detect the presence of 1-hydroxyphenazine and/or pyocyanin in a sample, but also assess the concentration of said phenazines present in said sample.

The method of the present invention allows analysing the phenazine content, in particular 1-hydroxyphenazine and/or pyocyanin, in different sample types, for example, samples of cell cultures, environmental samples such as water, soil or surface, and biological samples such as such as ear suppurations, skin exudates of burns or wounds, bronchial washes, saliva, blood or urine. In a particular embodiment of the in vitro method of phenazine detection and/or quantification, the sample comes from a subject who may have an infection caused by *Pseudomonas aeruginosa*. In a preferred embodiment, the sample is sputum. In another preferred embodiment, the sample is plasma.

In general, the assay sample shall be obtained by conventional methods, known by persons skilled in the art, depending on the nature of the sample. Before starting the assay, the sample may be subjected (or not) to a prior treatment, precipitated, fractionated, separated, diluted, concentrated or purified.

Any of a wide variety of immunochemical formats of analysis may be used according to the method of the present invention. Said immunochemical analysis techniques comprise, without being limited to, ELISA, lateral-flow immunoassay or LFIA, immunosensors, immunoaffinity extraction systems, immunoprecipitation, Western blotting, dot blot, radioimmunoassay, immunofluorescence, immunohistochemistry and flow cytometry. Said formats may be heterogeneous or homogeneous, sequential or simultaneous, competitive or non-competitive.

Heterogeneous immunoassay techniques typically involve the use of a solid phase material whereto the reaction product is bound, but it may be adapted to involve the binding of non-immobilized antigens and antibodies (i.e. an immunoassay in solution phase). The reaction product is separated from the excess sample, assay reagents and other substances, eliminating the solid phase of the reaction mixture (for example, by washing).

In a preferred embodiment of the method of phenazine detection and/or quantification of the invention, in particular 1-hydroxyphenazine and/or pyocyanin, the detection and/or quantification is performed using an ELISA-type assay (Enzyme Linked Immunosorbent Assay). This assay is based on the premise that an immunoreagent (e.g. an antigen or an antibody) is immobilized on a solid support, and, then, that system is placed in contact with a fluid phase containing the complementary reagent that may be bound to a marker compound. Thus, in a particular embodiment, the conjugate comprising an antigen derived from a phenazine of the invention is immobilized on the solid support, and this system is placed in contact with a sample susceptible of containing anti-phenazine antibodies. In particular, the conjugate which is immobilized on the support is the conjugate comprising PC1. In an alternative particular embodiment, the antibody of the invention is immobilized on the solid support, and this system is placed in contact with the sample susceptible of containing phenazine-type compounds.

Different types of ELISA are known, such as direct ELISA, indirect ELISA or sandwich-type ELISA, of competitive or non-competitive type.

In the direct competitive ELISA, the solid support whereon the assay is performed is prepared covering the surface of said support with the specific antibody. After a washing stage, the sample is added wherein it is suspected that the phenazine or phenazines of interest (or analyte) is found, and it is incubated together with the enzymatic marker bound to the hapten as competitor. This type of assay is indicative of the presence of analyte in the sample analysed. Samples of the same type as the test sample analyzed, but lacking the analyte of interest, are included as negative controls. It also includes positive controls, or samples wherein the analyte of interest is present.

In the indirect competitive ELISA, the support is prepared as in the previous way but this time immobilizing the antigen of interest. After the incubation and corresponding washing, the sample to be analysed and the specific antibody are added. It also includes positive and negative controls. The detection system uses two antibodies: a primary one against the antigen and a secondary one which recognizes the first and which is marked. The detection has greater sensitivity as it presents a signal amplification due to the binding of two or more secondary antibodies for each primary one. In this type of assay, a same marked secondary antibody and a same enzyme system make it possible to quantity a large variety of antigens.

In the coating antigen non-competitive ELISA, the antigen is immobilized on the solid support, in particular a conjugate according to the invention, then adding a first antibody which recognizes and is bound to the immobilized antigen. In the case of the direct non-competitive ELISA, the first antibody may be directly conjugated to a detectable labelling agent. Or in the case of the indirect non-competitive ELISA, a marked second antibody may also be added which recognizes the first antibody. In a particular embodiment of the invention, this assay makes it possible to assess the titer of antibodies generated in an immunized non-human animal by measuring the binding of serial dilutions of each serum to microtiter plates previously coated with a conjugate according to the invention, and the tracing of the different antibodies obtained and the antigens produced. In a preferred embodiment of the invention, the conjugate used comprises a hapten of formula I and BSA as carrier protein.

Methods included in the present invention are those ELISA assays wherein the conjugate of the invention is anchored to the support, and those ELISA assays wherein the antibody of the invention is anchored to the support.

In an embodiment of the invention, the immunoassay is an indirect competitive ELISA comprising:
(a) immobilizing, on a solid support, a conjugate comprising a hapten of formula I and a protein or a conjugate comprising a hapten of formula I and a polymer,
(b) eliminating the non-immobilized conjugate,
(c) adding the sample to be analysed and a first anti-phenazine antibody obtained on immunizing an animal with a conjugate comprising a hapten of formula I, or an antiserum containing the antibody, and a carrier protein which gives antigenicity in the solid support of section (a) and incubating,
(d) eliminating the first antibody not bound to the conjugate,
(e) adding a second antibody conjugated with a detectable labelling agent, said first antibody recognizing the first antibody and incubating,
(f) eliminating the second antibody not bound to the first antibody, and
(g) identifying and/or measuring the quantity of complex obtained according to section (e) with a composition containing a chromogenic, fluorogenic and chemiluminescent indicator substrate.

In the first stage of the method of the invention [stage (a)] a conjugate is immobilized on a solid support comprising a hapten of formula I and a carrier protein or a conjugate comprising a hapten of formula I and a polymer. It is possible to use any of a wide variety of solid supports in the immunochemical techniques of the present invention as previously described. In the context of the present embodiment, the solid support is plates for ELISA analysis. The immobilization of the conjugate on the surface of a support such as polystyrene plastic is directed by the surface chemistry. The immobilization capacity of the conjugates, which in this case act as competitive antigens, depends on many factors, such as time and temperature. The immobilization stage of the conjugate may include the blocking of the support spaces which have not been occupied by said conjugates. The blocking is carried out by proteins or detergents, preferably non-ionic detergents. With the aim of decreasing the non-specific interactions, the conjugate which is immobilized must comprise a protein different to that used in the conjugate used as immunogen. In a preferred embodiment, the conjugate immobilized in this stage comprises a hapten of formula I and a carrier protein, preferably BSA.

The components may be immobilized to the support by covalent bonds or by non-covalent bonds such as hydrogen bridges, hydrophobic interactions or ionic bonds. A general review of micromatrices and of suitable supports has been described in Shalon et al. (Genome Research 6: 639-645 (1996), LeGendre (BioTechniques 9: 788-805 (1990), U.S. Pat. Nos. 6,197,599 and 6,140,045. Alternatively, it is possible to use supports activated by epoxy groups, vinyl sulfonic groups, active ester groups, aldehyde groups, carboxyl groups, amino groups, thiol groups, isocyanate groups and similar. If the support is activated by epoxy groups, these groups include 3-glycidoxypropyltrimethoxysilane (GTMS), 2-(3,4 epoxycyclohexylethyl)trimethoxysilane, 3-glycidoxypropylmethyldiethoxysilane, 3-glycidoxypropyltriethoxysilane and similar.

Stage (b) of the method consists of eliminating the non-immobilized conjugate. Typically, this is carried by washings, typically between 1 and 10 washes, preferably from 2 to 5 washes. The washes have the purpose of eliminating the conjugates which have not been immobilized, so that everything which is detected is specific and desired.

The third stage of the method of the invention [stage (c)] consists of adding the sample to be analysed susceptible of containing the analyte which one wants to detect and/or quantify and a first anti-phenazine antibody according to the invention in the solid support of section (a) and incubating. This stage is the competitive stage of the assay. "First anti-phenazine antibody" is understood as an antibody according to the invention, generated against a conjugate comprising a hapten of general formula I and a carrier molecule which gives antigenicity, preferably against a conjugate comprising the mixture of PC1 haptens and the HCH carrier protein. The 1-hydroxyphenazine present in the sample to be analysed and the immobilized conjugate in the solid support of stage (a) shall compete for the binding of the first anti-phenazine antibody. As a person skilled in the art shall understand, the hapten of the immobilized conjugate of stage (a) and the hapten of the conjugate used for producing the antibodies of stage (c) must be the same. However, the second component of both conjugates, the carrier protein, may vary.

Stage (c) is the crucial stage of the assay. In a preferred embodiment, stage (c) has a duration between 10 minutes and 1 hour, preferably 30 minutes. The stirring during this stage favours the binding of the antibodies. For this reason, in a preferred embodiment, stage (c) is performed by stirring.

This assay has demonstrated tolerating a large range of ionic forces and pH values. The inventors have optimized the buffer used in the competitive stage of the assay [stage (c)]. In an embodiment of the invention, stage (c) is performed in the presence of a buffer which has the following characteristics:
  i. a concentration of non-ionic detergent between 0% and 2% preferably 0.05%;
  ii. a pH between 3 and 10, preferably 7.5;
  iii. a conductivity between 5 and 70 mS/cm, preferably 14.5 mS/cm.

The fourth stage of the method of the invention [stage (d)] consists of eliminating the first antibody not bound to the immobilized conjugate. Typically, this is performed by washings in the same conditions as stage (b).

The following stage of the method of the invention [stage (e)] consists of adding a second antibody conjugated with a detectable labelling agent, said first antibody recognizing the first antibody and incubating. Said second antibody is conjugated with a compound capable of reacting with a substrate, so that a chromogenic, fluorogenic and/or chemiluminescent detection is derived from it. This compound may be bound to the antibody directly or through another component. The second antibody may be a natural immunoglobulin isolated from a non-human species different to the species used to produce the first antibody (for example, anti-mouse IgG antibody, anti-goat IgG antibody, anti-goat IgM antibody) or it may be produced recombinantly or synthetically. It may be an immunoglobulin or a fragment of immunoglobulin (for example, FAb, F[Ab]2). As desired, other binding molecules may be used together with or instead of said second antibodies. In a preferred embodiment, the second antibody is conjugated with an enzyme, preferably peroxidase, more preferably HRP. The suitable conditions for which the binding of the second antibody to the first antibody takes place are known by persons skilled in the art.

Then, stage (f) takes place consisting of eliminating the second antibody not bound to the first antibody. Typically, this is performed by washing in the same conditions as in stages (b) and (d).

Finally, the last stage (g) consists of the identification and/or measuring of the quantity of the complex obtained according to section (e) with a composition containing a chromogenic, fluorogenic and chemiluminescent indicator substrate. An indicator substrate is a substance capable of reacting with a labelling agent of the second antibody giving as a result a chromophore, fluorescent or chemiluminescent material which may be detected by methods known in the state of the art. Suitable indicators substrates to carry out the present invention are known by persons skilled in the art and accessible from various commercial sources. Preferably, the indicator substrate is chromogenic, such as, for example 3,3',5,5'-tetramethylbenzidine (TMB), azino-bis(3-ethylbenzothiazoline 6-sulfonic) acid or phenyldiamine, without limitation of using other substrates as chemical markers (for example, colloidal gold markers, latex balls). When chromogenic substrates are used, the presence of 1-hydroxyphenazine in the sample is demonstrated by the appearance of a colour whose intensity varies directly with the number of molecules bonded to the first anti-phenazine antibody added in stage (c) and its quantification may be carried out, for example, by means of spectrophotometry. If a fluorogenic substrate is used, the detection and quantification are performed by means of fluorometry and if the substrate is chemiluminescent, the signal may be quantified by means of a luminometer.

In a particular embodiment of the invention, the enzyme marker is horseradish peroxidase (HRP), the substrate is chromogenic and the reaction is enzymatic. In this case, the reaction is inhibited after a time since the substrate was added and for this the optimum operating conditions of the enzyme being used are changed.

In a preferred embodiment of the previous in vitro method, when the detection and/or quantification of phenazine comprises the detection of pyocyanin, prior to stage (c) of placing the sample in contact with the anti-phenazine antibody, said method further comprises a stage (c') consisting of the conversion of pyocyanin into 1-hydroxyphenazine by means of suitable chemical or biological agents and known by an average person skilled in the art, such as the treatment in base medium, such as for example, NaOH, or enzyme treatment.

In a particular embodiment, the sample is divided into two parts. A fraction (A) shall be used to quantify the quantity of 1-hydroxyphenazine present initially in the sample, and it will be added directly in stage c) and the second fraction (B) shall undergo prior treatment (stage c') in which the pyocyanin becomes 1-hydroxyphenazine. The immunochemical quantification of fraction A shall give us the initial value of 1-hydroxyphenazine present in the sample and the difference between fraction B and fraction A shall correspond to the pyocyanin concentration in the sample.

Kit for the Detection and/or Quantification of Phenazine Compounds of the Invention In another aspect, the present invention relates to a kit for the detection and/or quantification of phenazine compounds, in particular 1-hidoxyphenazine and/or pyocyanin, in the sample of a subject comprising at least one component selected from the group formed by an antibody according to the invention, an antiserum comprising an antibody according to the invention and a conjugate according to the invention.

In a particular embodiment of the kit according to the invention, the antibody or the conjugate is immobilized on a solid support, as described above.

In an even more preferred embodiment, the kit further comprises an antibody against the anti-phenazine antibodies according to the invention.

All the particular embodiments of the conjugates and antibodies of the present invention are also applicable to the kits of the invention.

This type of devices make it possible to perform diagnostic tests outside of a clinical laboratory and by non-specialized personnel, automatically and in miniaturized form, from samples of a small volume and easy production.

The following examples serve to illustrate the invention and should not be considered, in any case, as limiting of the scope thereof.

EXAMPLES

The compounds of formula I may be prepared following different methods known by any person skilled in the field of organic synthesis, in particular using general processes that are shown in the following schemes. The starting materials for the preparative methods are commercially available or may be prepared by methods described in the literature.

1. Material and Methods

A. Chemical

General Methods and Instrumentation.

The thin-layer chromatography was performed on F254 aluminium sheets (0.25 mm) precoated with 60 silica gel (Merck, Darmstadt, Germany), and the separations of the different synthesized compounds was performed by silica column chromatography with 60 A D.C. 35-70 μm sodium dodecyl sulfate. The NMR $^1$H spectrums were obtained with a Varian Inova-500 (Varian Inc., Palo Alto, Calif.) spectrometer (500 MHz for $^1$H. The exact mass was obtaining using the Waters Acquity high-performance liquid chromatography system (UPLC) (Waters Corp., Milford, Mass., EE.UU.), using as detector Waters LCT Premier XE mass spectrometer, flight time mode ESI(+). A UPLC Acquity C18 2.1×100 mm column was used (7 μm; Waters; Massachusetts, USA). The HPLC-UV analysis was carried out using the LaChrom Elite L-2130 HTA pump with a L-2455 array diode detector and L-2200 automatic sampler (Merck, Darmstadt, Germany). The chromatograms were processed with EZChrom Elite software (Merck, Darmstadt, Germany). A Lichrosphere 100 RP-18 Encaped 125×4 column was used (5 μm; Merck; Darmstadt, Germany). The analyses were performed in gradient mode and the following program was used as mobile phase: min 0-2, ACN: aqueous buffer (0.3% $NH_3$, $H_2O$ (adjusted to pH=9 with HCl)) 0:100; min 18, ACN: aqueous buffer 50:50, at a flow of 1.0 mL min$^{-1}$.

1-Hydroxyphenazine. 1-hydroxyphenazine was synthesized following the synthesis described by Vivian (*Nature* 1956, 178, 753). A yellow powder was obtained with a 94% yield. $^1$H-NMR (500 MHz, $CDCl_3$); δ ppm:7.20 (dd, $1H_{Ar}$, J=1.5 Hz, J=7.4 Hz), 7.69 (dd, $1H_{Ar}$, J=1.5 Hz, J=8.7 Hz), 7.78 (dd, $1H_{Ar}$, J=7.2 Hz, J=8.7 Hz), 7.94 (m, $2H_{Ar}$), 8.21 (m, $1H_{Ar}$), 8.29 (m, $1H_{Ar}$) UPLC ESI(+) calculated for $C_{12}H_8N_2O$(M+) 196.0637. found 197.0696.

1-Hydroxyphenazine from Pyocyanin

A 2M NaOH solution (250 μL) was added to a vial containing pyocyanin (10 mM, 25 μL) in 10 mM PBS (85 μL), previously spiked with phenazine (500 μM, 140 μL). The progress of the reaction was monitored by extracting aliquots (10 μL) from the reaction solution at various time intervals, diluting them with 250 mM PBS (90 μL) and adding 1 M HCl (10 μL) to neutralize the pH.

Pyocyanin. Pyocyanin was obtained from 1-hydroxyphenazine by the selective methylation of N5 in order to obtain the blue toxin following the process already described by Surrey (Organic Syntheses Collective 1955, 3, 753-756) to obtain the desired compound with 53% yield. UPLC ESI(+) calculated for $C_{13}H_{10}N_2O$(M+) 210.0793. found 211.0862.

Synthesis of the PC1 Hapten.

The immunization haptens and competitors were synthesized by the method described by Surrey, stated above, with slight modifications.

1:3 mixture of methyl 9-methoxyphenazine-2-carboxylate and methyl 6-methoxyphenazine-2-carboxylate (3)

3,4-diaminobenzoic acid (2 g, 13.14 mmol) was converted into 3,4-methyl diaminobenzoate 2 (2.04 g, 12.27 mmol, 94% yield) using thionyl chloride (1.24 mL, 17.1 mmol) with a MeOH reflux during 11 h. In parallel, a solution of 3-methoxycatechol (2 g, 14.27 mmol) was oxidized by the drop by drop addition of a o-chloranil solution (3.65 g, 14.84 mmol) in anhydrous $Et_2O$ at −20° C. during 15 minutes to obtain by filtration 3-methoxy-[1,2]benzoquinone 1 (1.56 g, 11.29 mmol, 79% yield) as a dark green solid. The solid was washed with $Et_2O$ and the final residue obtained (700 mg, 5.06 mmol) was immediately redissolved in $CH_2Cl_2$ (30 mL) and it was added drop by drop to a solution of methyl ester 2 (660 mg, 3.97 mmol) in the same solvent (10 mL) slightly acidified with acetic acid (5 drops). After stirring during 1.5 h at a.t., the solution was diluted with water (20 mL) and was extracted with $CH_2Cl_2$ (10 mL), it was dried ($Mg_2SO_4$) and the solvent was vacuum eliminated. The product was purified using silica gel chromatography in a mobile phase of 1:1 EtOAc:hexane to produce the desired compound in the form of a mixture of isomers in the form of a yellow solid (110 mg, 41% yield). Maj is majority product and Min minority product. $^1$H-NMR (500 MHz, $CDCl_3$); δ ppm: 4.03 (s, 6H, 1-$COOCH_3$ $_{maj}$, 1-$COOCH_3$ $_{min}$), 4.18 (s, 6H, 1-$OCH_3$ $_{maj}$, 1-$OCH_3$ $_{min}$), 7.07 (d, $1H_{Ar\ min}$, J=6.59 Hz), 7.1 (d, $1H_{Ar\ maj}$, J=7.6 Hz), 7.73-7.86 (complete signal, 4H, $2H_{Ar\ min}$, $2H_{Ar\ maj}$), 8.36 (dd, $1H_{Ar\ maj}$, J=9.03 Hz, J=1.7 Hz), 8.38 (dd, $1H_{Ar\ min}$, J=overlapped), 8.23 (dd, $1H_{Ar\ min}$, J=9.03, J=1.7), 8.42 (dd, $1H_{Ar\ maj}$ J=9.03, J=1.7), 8.95 (s, $1H_{A\ maj}$), 9.15 (s, $1H_{A\ min}$).

1:4 mixture of methyl 9-hydroxyphenazine-2-carboxylate and methyl 6-hydroxyphenazine-2-carboxylate (4)

A solution of the 1:3 mixture of methoxyphenazine carboxylates 3 (81 mg, 0.30 mmol) in anhydrous $CH_2Cl_2$ (2 mL) was cooled to −75° C. and it was added to a solution of 1 M boron tribromide in $CH_2Cl_2$ (410 μL, 0.41 mmol). After stirring during 15 min, the reaction mixture was left to cool at ambient temperature and was then stirred during a further 10 h. Later, the reaction flask was immersed in an ice bath (0°-4° C.) and distilled water was added drop a drop, until the excess tribromide was destroyed. The residue was extracted later with $CH_3Cl$ (2 mL), it was dried ($Mg_2SO_4$) and the solvent was vacuum eliminated. Silica gel chromatography was used to purify the reaction mixture producing the desired isomer mixture 4 as a red/brown solid (23 mg, 10% yield). Maj means majority product and Min minority product. $^1$H-NMR (500 MHz, $CDCl_3$); δ ppm: 4.05 (s, 6H, 2-$OCH_3$ $_{maj}$, 2-$OCH_3$ $_{min}$), 7.76-7.85 (sc, $2H_{D-F\ maj}$, $2H_{D-F\ min}$)) 8.23 (d, $1H_{B\ maj}$, J=9.0), 8.28 (d, $1H_{B\ min}$, J=9.0 Hz), 8.37 (dd, $1H_{C\ maj}$, J=9.03 Hz, J=1.71 Hz), 8.39 (dd, $1H_{C\ min}$, J=9.03 Hz, J=1.71 Hz), 8.92 (s, $1H_{A\ min}$), 8.98 (s, $1H_{A\ maj}$)

1:4 mixture of 9-hydroxyphenazine-2-carboxylic acid and 6-hydroxyphenazine-2-carboxylic acid (5) (1:4 mixture PC1 haptens)

The 1:4 mixture of hydroxyphenazine carboxylates 4 (20 mg, 78.7 mmol) was dissolved in a 0.5 M KOH solution in THF (1 mL) and was stirred during 30 min at a.t. Later, the THF was eliminated by distillation and the aqueous part was washed with a saturated solution of $NaHCO_3$ (5 mL) and EtOAc (5 mL×3 times). The yellow aqueous phase was acidified at pH 3 with 5N HCl and it was extracted with EtOAc (3×5 mL). The combined organic extracts of EtOAc were dried on $Mg_2SO_4$ and the solvent was vacuum eliminated until dry. The resulting orange powder was washed with $Et_2O$ (5 ml) and it was filtered through a filter plate to give a 1:4 mixture of the expected hapten 5 (13 mg, 97% yield) as a 1:4 mixture of positional isomers. Maj means majority product and Min minority product. $^1$H-NMR (500 MHz, DMSO); δ ppm: 7.25 (d, $1H_{D\ min}$, J=7.84 Hz), 7.27 (d, $1H_{D\ maj}$), 7.73 (d, $1H_{F\ min}$, J=overlapped), 7.75 (d, $1H_{F\ maj}$, J=8.33), 7.84 (dd, $1H_{E\ maj}$, J=7.48 Hz, J=8.76 Hz), 7.7 (dd, $1H_{E\ min}$, J=7.42 Hz, J=8.88 Hz), 8.28-8.33 (d, $1H_{C\ min}$, J=overlapped), 8.29 (dd, $1H_{B\ min}$, J=8.7 Hz, J=overlapped), 8.32 (dd, $1H_{B\ maj}$, J=9.05 Hz, J=1.7), 8.36 (d, $1H_{C\ maj}$, J=9.09 Hz), 8.77 (s, $1H_{A\ maj}$), 8.81 (s, $1H_{A\ min}$). UPLC ESI(+) calculated for $C_{13}H_8N_2O_3$ (M+) 241.0613, found 241.0606.

B. Immunochemistry

General Methods and Instrumentation.

The MALDI-TOF-MS mass spectrometer (mass spectrometer with laser assisted by ionization/desorption matrix with flight time) which it uses to characterize the conjugates of protein was a Bruker 200-Hz SmartBeam (Bruker-Daltonics, Leipzig, Germany). The detection was performed in the positive ion mode, ionized with a laser power set at 70% of the maximum laser intensity of the instrument at a frequency of 10-100 Hz. The pH and the conductivity of all the buffers and solutions was measured with a 540 GLP phMeter and a LF 340 conductivity meter, respectively (WTW, Weilheim, Germany). The polystyrene microtiter plates were from Nunc (Maxisorp, Roskilde, Denmark). The washing steps were carried out using a microplate washer (ELx405 HT (BioTek, Vinooski, Vt., USA)). The absorbencies were read in a SpectramaxPlus (Molecular Devices, Sunnyvale, Calif.) in a wavelength mode of 450 nm. The competition curves were analysed with a four-parameter equation using the SoftmaxPro v4.7 (Molecular Devices) and GraphPad Prism v 4 (GraphPad Software Inc, San Diego, Calif.) software. The standard curve was adjusted to a logistical equation of four parameters according to the formula $y=(A-B/[1-(x/C)D])+B$, where A is the maximum absorbance, B is the minimum absorbance, C is the concentration which produces 50% of the difference between the maximum and minimum absorbance (or $IC_{50}$), and D is the gradient in the point of inflection of the sigmoidal curve. Unless indicated otherwise, the data shown correspond to the mean of at least two replicates.

Buffers

PBS is a 140 mM saline solution in a 10 mM phosphate buffer and, unless indicated otherwise, the pH is 7.5. PBST is PBS with 0.05% Tween 20. PBhST is PBST with a 280 mM saline solution. The hydrolysis buffer is 237 mM of phosphate buffer with 50 mM of saline solution and the pH is 7.5. hPB is 250 mM phosphate buffer and the pH is 7.5. hPBT is hPB, with 0.1% Tween 20. The coating buffer is 50 mM carbonate-bicarbonate pH=9.6. Citrate buffer is a 40 mM sodium citrate solution, pH=5.5. Borate buffer is 0.2 M of boric acid/sodium borate, pH=8.7. The substrate solution contains 0.01% TMB (3,3',5,5'-tetramethylbenzidine) and 0.004% $H_2O_2$ in citrate buffer.

Immunoreagents

Immunogens: PC1-HCH

The PC1 hapten was coupled to horseshoe crab hemocyanin (HCH) following the mixed anhydride method (MA). The carboxylic acid of the PC1 hapten (1.2 mg, 5 μmol) was activated with isobutyl chloroformiate (0.77 μL, 6 μmol) in the presence of tributylamine (1.3 μL, 5.5 μmol) in anhydrous DMF (dimethylformamide, 100 μL) under argon atmosphere and in an ice bath during 30 minutes. The activated hapten was added drop by drop to a HCH solution (5 mg) in borate buffer (900 μL). The mixture was stirred for 3 hours at ambient temperature and later during the night at 4° C. The conjugate was dialyzed against 0.5 mM PBS (4×5 L) and the final quantity of protein recovered after dialysis was quantified by Bradford protein assay. The conjugate was taken to 2 mg/mL in 10 mM PBS, it was aliquoted and stored at −80° C. The working aliquot was maintained at 4° C.

Bioconjugates: PC1-BSA,

They were prepared using the active ester method (AE) by activation of the hapten (1.2 mg, 5 μmol) with N-hydroxysuccinimide (NHS, 1.44 mg, 6 μmol) and dicyclohexylcarbodiimide (DCC, 5.2 mg, 6 μmol) in anhydrous DMF 100 μL) and stirring during one hour at ambient temperature. The suspension was centrifuged at 10000 rpm during 10 min and the supernatant was added drop by drop to a BSA solution (bovine serum albumin, 10 mg) in, borate buffer (1.8 mL) and it was stirred during 4 h at a.t. The conjugate was dialyzed and stored. Alternatively, bioconjugates of PC1-BSA were prepared by the mixed anhydride method, which were prepared in parallel to the PC1-HCH conjugates.

Analysis of Hapten Density.

The hapten densities of the bioconjugates were calculated measuring the molecular weight (MW) of the native proteins in comparison with those of the conjugates by MALDI-TOF-MS analysis. In this sense, the MALDI spectrums were obtained by the mixture of 2 μL of the recently prepared matrix (trans-3,5-dimethoxy-4-hydroxycinammic acid, 10 mg/mL, in $CH_3CN/H_2O$ 70:30, 0.1% formic acid) with 2 μL of a solution of the conjugates or of the proteins in $CH_3CN/H_2O$ 70:30, 0.1% formic acid (10 mg/mL). The hapten density (δ hapten) was calculated according to the following equation: {MW(conjugate)−MW(protein)}/MW(hapten)}.

The coupling efficacy assessed by MALDI-TOF-MS of the immunoreagents corresponding to a hapten density of 20 for the PC1-BSA (MA) conjugate and 10 for PC1-BSA (AE).

Polyclonal Antiserums.

The polyclonal antiserums As230, As231 and As232 were obtained by the immunization of New Zealand white rabbits (female) with weights around 1-2 kg with PC1-HCH (MA) following a protocol already described by Ballesteros et al. (*Analytica Chimica Acta* 1997, 347, 139). The evolution of the titers of antibodies was assessed by measuring the binding of serial solutions of each antiserum to microtiter plates coated with the homologous BSA conjugate. Once acceptable titers of antibodies are obtained, the animals were exsanguinated and the blood was collected in Vacutainer tubes provided with serum separation gel. The antiserums were obtained by centrifugation and were stored at −80° C. in the presence of 0.02% $NaN_3$.

After carrying out two-dimensional titration assays (indirect non-competitive ELISA) the appropriate dilutions were established of the antiserums and the coating antigens for the indirect competitive ELISA. The best combination was As230/PC1-BSA (AE).

Indirect Competitive ELISA As230/PC1-BSA (AE) for 1-Hydroxyphenazine

Non-Hydrolyzed Samples

The microtiter plates were coated with PC1-BSA (AE) (0.125 μg/ml with coating buffer 100 μL/well) during 4 h at 25° C. with adhesive sealants. Then, the plates were washed four times with PBST (300 μL/well) before adding the standards (1-hydroxyphenazine or another type of related analytes, at different concentrations from 1000 nM to 0 nM in PBhST), and the samples at different concentrations (50 μl/well), followed by the As230 antiserum solution (1/8000 dilution in PBhST, 50 μl/well). After 30 min at ambient temperature, the plates were washed a further nine times with PBST and the anti-IgG-HRP solution was added (1/6000 in PBST, 100 μl/well). After 30 min of incubation at ambient temperature, the microplates were again washed four times with PBST and the substrate solution was added (100 μl/well) and the enzyme reaction was stopped after 30 min at ambient temperature by $H_2SO_4$ 4 N (50 μl/well). The absorbencies were measured at 450 nm. The standard curve was adjusted to a logistical equation of four parameters according to the formula $y=(A-B/[1-(x/C) D])+B$, where A is the maximum absorbance, B is the minimum absorbance, C is the concentration that produces 50% of the difference between the maximum absorbance and minimum absorbance of the absorbance (or $IC_{50}$), and D is gradient in the point of inflection of the sigmoidal curve. The limit of detection (LOD) is defined as the concentration which gives 90% response of the maximum absorbance ($IC_{90}$) (see FIG. 1 and table 1).

Hydrolyzed Samples

The process is the same described for the non-hydrolyzed samples, using microtiter plates coated with PC1-BSA (0.25 μg/ml in coating buffer 100 μL/well) during 4 hours at 25° C., and then the PC1 standards, (of 3200 nM at 0 nM in hydrolysis buffer) and the samples (diluted in a hydrolysis buffer) were added to the microplates followed by the As230 solution (1/6000 diluted in hPBT, 50 μl/well). The following steps, washing, anti-IgG-HRP and the addition of substrate solution, are the same described for the non-hydrolyzed samples (see FIG. 1 and table 1).

TABLE 1

Parameters of the ELISA As230/PC1-BSA (AE) assay in buffer, in sputum[a] and in plasma[g].

| | | Non-hydrolyzed samples | Hydrolyzed samples | | |
|---|---|---|---|---|---|
| | | | | Sputum | Plasma |
| | | PBST[c] | Sputum diluted 1/20 in PBST[d,e] | Hydrolysis buffer[f] | diluted 1/20 in PB 250 mM[d,e] | diluted 1/20 in PB 250 mM[d,e] |
| Parameters of the assay | Amax | 0.78 ± 0.03 | 0.78 ± 0.09 | 0.85 ± 0.04 | 0.83 ± 0.04 | 0.84 ± 0.01 |
| | Amin | 0.18 ± 0.03 | 0.11 ± 0.01 | 0.10 ± 0.01 | 0.09 ± 0.01 | 0.11 ± 0.01 |
| | Slope | −0.87 ± 0.04 | −0.67 ± 0.03 | −0.69 ± 0.01 | −0.71 ± 0.01 | −0.62 ± 0.07 |
| | IC50[b] | 0.53 ± 0.04 | 14.4 ± 0.05 | 0.8 ± 0.01 | 11.2 ± 0.03 | 5.6 ± 0.07 |
| | IC90 (LOD)[b] | 0.01 ± 0.01 | 0.4 ± 0.01 | 0.04 ± 0.01 | 0.60 ± 0.01 | 2.4 ± 0.01 |
| | $R^2$ | 0.992 ± 0.003 | 0.995 ± 0.004 | 0.997 ± 0.003 | 0.997 ± 0.003 | 0.994 ± 0.002 |

[a]The sputum is a pool of sputa of 10 individuals not infected with *P. aeruginosa*;
[b]all the concentrations are expressed in nM;
[c]The data correspond to a mean of n = 3, where each measurement is made in triplicate;
[d]The data shown are the mean and the standard deviation of at least two replicated wells;
[e]The concentration values have been multiplied by twenty, to provide the real detectability value of the source sample, bearing in mind the dilution factor applied before the analysis to avoid the interferences caused by the matrix;
[f]the concentration values have been multiplied by two, to provide the real detectability in the original sample, before the hydrolysis.
[g]The plasma is a pool of plasma of 10 individuals not infected with *P. aeruginosa*.

Cross-Reactivity Determinations.

Stock solutions were prepared of different compounds structurally related with pyocyanin and 1-hydroxyphenazine (10 mM in dimethyl sulfoxide) and they were stored at 4° C. The calibration curves were prepared in PBST and were executed in the ELISA following the above protocol. The cross-reactivity values were calculated according to the following equation (IC50 1-hydroxyphenazine [nM]/IC50 phenazine compounds [nM])×100 (Table 2)

TABLE 2

Cross-reactivity of phenazine compounds in the ELISA As230/PC1-BSA (AE) assay

| Compound | ELISA $IC_{50}$ (nM) | % RC |
|---|---|---|
| 1-hydroxyphenazine | 0.62 | 100 |
| Pyocyanin | >800 | <0.1 |
| Phenazine | >800 | <0.1 |
| Phenazine-2-carboxylic acid | >800 | <0.1 |
| Methyl 5-methylphenazine sulfate | 140 | 0.4 |

Sputum Samples

Sputa of 10 patients diagnosed with not having *P. aeruginosa* infection were processed in the Institut de Recerca of the Vall d'Hebron hospital following the protocol described by the same group Clinical & Experimental Allergy 2012, n/a-n/a. The recovery of this process was evaluated, for this reason sputa were spiked (150 mg) with 1-hydroxyphenazine (25 mM) and once the sputum was processed, the quantity of 1-hydroxyphenazine of the supernatant was quantified by the ELISA As230/PC1-BSA (AE) after the sputum treatment. A pool of blank sputa was prepared from the mixture of sputum supernatants of 10 persons not infected by *P. aeruginosa*. The pool of sputa was used for the matrix effect studies, the evaluation of hydrolysis treatment and precision studies.

Plasma Samples

A pool of blank plasmas was prepared from the mixture of the plasma supernatants of 10 persons not infected by *P. aeruginosa*. The pool of plasmas was used for the matrix effect studies and assessment of the hydrolysis treatment.

Hydrolysis of Sputum Samples

10 M NaOH (100 μL) was added to the sputum supernatant (900 μL) and the mixture was stirred during 20 min, it was neutralized with 10 M HCl (100 μL) and was diluted 20 times with hPB.

Hydrolysis of Plasma Samples

10 M NaOH (100 μL) was added to the plasma supernatant (900 μL) and the mixture was stirred during 20 min, it was neutralized with HCl (100 μL) and was diluted 5 times with hPB.

Sputum Matrix Effect Studies

The non-specific interferences produced by the sputum have been evaluated for preparation of the sputum standard calibration curve (native or hydrolyzed) at various dilution factors (1/5, 1/10, 1/20) and being subsequently analysed by ELISA to compare the parallelism with the standard curve prepared in PBhST buffer or in hydrolysis buffer, respectively (see FIG. 1 and table 1).

Plasma Matrix Effect Studies

The non-specific interferences produced by the plasma have been evaluated for preparation of the sputum standard calibration curve (native or hydrolyzed) at various dilution factors (1/2, 1/5, 1/10, 1/20) being subsequently analysed by ELISA (see table 1).

Precision Studies

To assess this parameter, spiked blind samples were prepared at different analyte concentrations and were later measured by ELISA in the corresponding calibration curve. The measurements were made in triplicate using as standard curve in an appropriate dilution of the analyte in the corresponding buffer. Samples of non-hydrolyzed buffer. 7 blind samples in spiked PBS were prepared at different concentrations of 1-hydroxyphenazine and they were measured without dilution in the ELISA standard curve (see FIG. 2 (top)). Samples of hydrolyzed buffer. 14 blind samples were prepared in PBS. 7 of them spiked at different concentrations of 1-hydroxyphenazine and the 7 remaining ones spiked at different concentrations of pyocyanin. All samples underwent hydrolysis treatment, 10M NaOH (100 μL) was added to the blind samples (900 μL) and the mixture was stirred during 20 minutes. It was then neutralized with 10M HCl 10M (100 μL) and the samples were diluted to 1/2 with hPB. Finally, the samples were measured in the corresponding standard curve (see FIG. 2 (bottom). Samples of non-hydrolyzed sputum. The process was the same as that described for the samples of non-hydrolyzed buffer, in this case 4 blind samples of 1-hydroxyphenazine were prepared at different spiked concentrations in blank sputum. Once the samples were prepared, they were diluted 20 times with PBhST and they were measured in the corresponding standard curve of the ELISA. Samples of hydrolyzed sputum. The process was the same as that described for the samples of hydrolyzed buffer, in this case 9 blind samples of spiked pyocyanin were prepared in blank sputum. Once prepared, the samples were hydrolyzed and diluted 20 times with hPB and they were measured in the corresponding standard curve of the ELISA (see table 3).

TABLE 3

Results of the recovery studies of the ELISA As230/PC1-BSA (AE) assay performed in sputum[a].

|  | Spiked concentration | Measured concentration[b] | Recovery (%) |
|---|---|---|---|
| pyocyanin | 2.5 | 2.34 ± 0.37 | 94 |
|  | 5 | 4.25 ± 1.15 | 85 |
|  | 50 | 55.57 ± 7.5 | 111 |
|  | 250 | 179.63 ± 17.17 | 72 |
|  | 500 | 555.66 ± 88.49 | 110 |
|  | 1000 | 1035.88 ± 25.39 | 103 |
|  | 10000 | 7219.19 ± 829.25 | 72 |
|  | 50000 | 50146.19 ± 1685.17 | 100 |
|  | 100000 | 72434.53 ± 1347.23 | 73 |
| 1-hydroxyphenazine | 0.5 | 0.48 ± 0.05 | 96 |
|  | 5 | 4.32 ± 0.56 | 86 |
|  | 50 | 51.66 ± 2.38 | 103 |
|  | 250 | 246.09 ± 43.14 | 98 |

[a] The sputum samples were prepared using a pool of sputa from healthy individuals, they were then spiked with 1-hydroxyphenazine or pyocyanin, treated as described in the section on Hydrolysis of Sputum Samples and measured by ELISA in the corresponding calibration curve. All concentrations were expressed in nM;
[b,d] The results shown are the mean and standard deviation of at least three replicated wells.

Results

A new immunochemical assay has been developed to detect 1-hydroxyphenazine and pyocyanin using the antibodies targeted against 1-hydroxyphenazine. Pyocyanin only differs from 1-hydroxyphenazine in the methyl group of N5. A simple hydrolysis treatment allows the elimination of the methyl group of pyocyanin to convert into 1-hydroxyphenazine, which allows quantification of both analytes using a single antibody.

The mixture of PC1 haptens obtained was used to prepare the immunogen (PC1-HCH) with the aim of generating antibodies against 1-hydroxyphenazine. The affinity of the antibodies obtained (As230-As232) against the PC1-BSA bioconjugates (AE and MA) was assessed using immunochemical competence assays with the intention of ascertaining the most suitable conditions. As a result of these experiments, five competitive immunoassays were obtained, of which the As230/PC1-BSA antiserum/bioconjugate (AE) combination showed the best parameters and was, therefore, chosen for later studies. The assay chosen is stable between pH 5 and pH 9.5, neither is it significantly affected by the Tween 20 content, but with a high concentration of salts in the assay buffer the ELISA provides an improvement in terms of detectability and, for this reason, the assay buffer contains a salt concentration of 280 mM (conductivity of 27.2 mS cm-1). In the established conditions, samples of 1-hydroxyphenazine in buffer may be analysed in 1.30 h with a limit of detection of 0.01±0.01 nM (N=3, see table 1 and FIG. 1).

Assay Conditions

Figure 2:
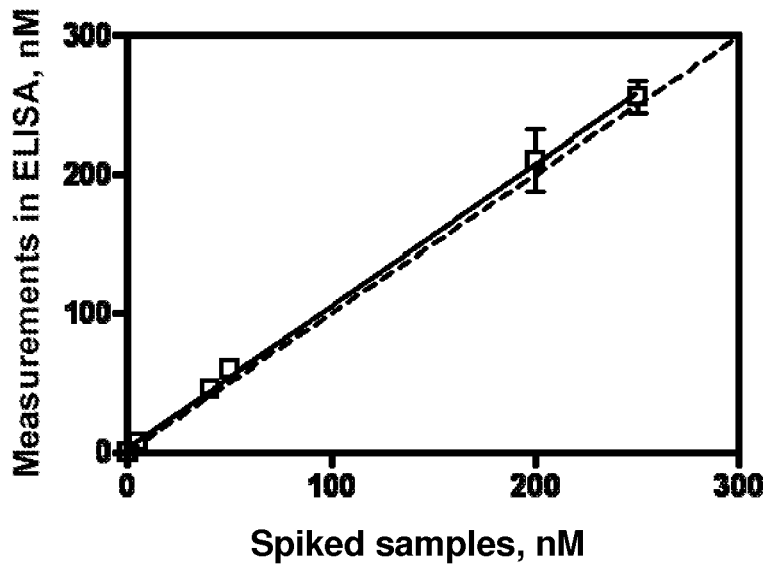
FIG. 2. The precision was assessed by the analysis of spiked samples of pyocyanin and 1-hydroxyphenazine in buffer. Top: shows the precision studies of 1-hydroxyphenazine in PBST [Legend: □ 1-hydroxyphenazine, y=(1.03±0.02)x+(3.05±2.55), $R^2$=0.992]. Bottom: Shows the precision studies of spiked samples of 1-hydroxyphenazine and pyocyanin in buffer and quantified after the hydrolysis treatment [Legend: □ 1-hydroxyphenazine, y=(0.94±0.05)x−(3.66±6.23), $R^2$=0.953; Δ Pyocyanin and =(0.97±0.05)x−(3.42±6.40), $R^2$=0.943]. The data shown are the mean and the associated error of three wells of replicate.
Figure 2:
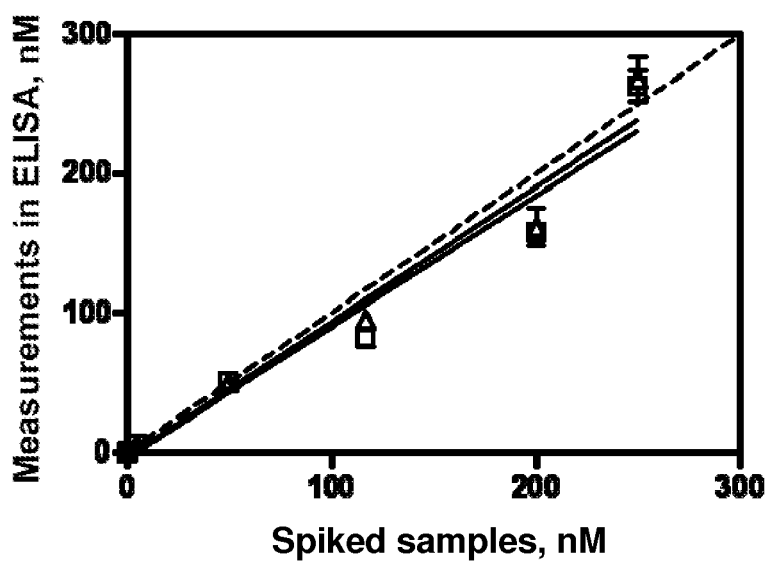

Specificity studies demonstrated that the assay was highly specific for 1-hydroxyphenazine (see table 2). Other phenazines showed a cross-reactivity less than 0.1%, including pyocyanin. Therefore, it was necessary to develop a simple method to convert pyocyanin in 1-hydroxyphenazine with a good yield. This could be achieved by treating pyocyanin solutions with 1 M NaOH during 20 min at a.t. The hydrolysis of the methyl group was controlled by HPLC-UV using phenazine as internal standard and the results demonstrated that the conversion is quantitative in these conditions. As shown in FIG. 2 (bottom), a good correlation was observed ($R^2=0.943$) between the sample measurements and the spiked samples for the detection of pyocyanin once hydrolyzed.

Therefore, both 1-hydroxyphenazine and pyocyanin of a specific sample can be measured simultaneously. To do this, the sample is divided in two parts, one of them is directly used for the immunochemical quantification of 1-hydroxyphenazine, whilst the second fraction is hydrolyzed before the analysis, with the aim of converting in 1-hydroxyphenazine using the process described above; they were then analysed by ELISA to obtain the total content of 1-hydroxyphenazine. The difference between these two measurements will correspond to the pyocyanin concentration in the sample.

The studies aimed at assessing the possible non-specific interferences caused by the hydrolysis process in the ELISA showed that these effects were negligible and could be corrected by slightly changing the assay conditions. Therefore, after treatment with NaOH and the later addition of HCl, the samples were diluted with 250 mM borate buffer with the aim of buffering the samples and minimizing the salt concentration, since said parameters influence the ELISA measurements. Bearing in mind the quantitative conversion of pyocyanin in 1-hydroxyphenazine, pyocyanin may be detected in a buffer with a LOD value of 0.04±0.01 nM (N=3). For both cases, the quantification of 1-hydroxyphenazine and pyocyanin in buffer, was exact as can be observed in FIG. 2, where it shows the correlation studies between the spiked samples and the measurements obtained in the ELISA. The gradient of the regression analysis is always close to 1, and the regression coefficients are also good for both analytes.

Determinations in Sputum Samples

Since the patients infected by *P. aeruginosa* have high concentrations of pyocyanin in their sputa, this methodology was applied to the analysis of the sputum samples.

Thus, sputum samples were obtained from patients not infected by *P. aeruginosa* and they were grouped to investigate the possible non-specific interferences caused by the matrix. In first place, the sputum samples were treated as described in the experimental section, they were diluted with the assay buffer several times, and the different dilutions of the samples were used to assess interferences in the ELISA. Both the intact sputum and the hydrolyzed sputum samples did not significantly interfere in the assay. A 20× dilution with PBST or with the hydrolysis buffer was found to be sufficient to avoid the interferences caused by the sputum components (see FIG. 1 and table 1). Bearing in mind the dilution factor applied, 1-hydroxyphenazine and pyocyanin may be analysed in sputum samples with a LOD of 0.4±0.01 nM (N=3), and 0.6±0.01 nM (N=3), respectively.

Finally, a set of blind sputum samples were prepared using the pool of sputum from healthy individuals. The sputum samples were spiked with 1-hydroxyphenazine and pyocyanin, the pyocyanin samples were hydrolyzed and they were quantified by ELISA. As can be observed in Table 3, the recoveries were good in both cases, a fact that demonstrates that the immunochemical process developed is capable of quantifying the analytes in this type of samples quickly and efficiently.

Determination in Plasma Samples

Due to the importance of being able to detect the presence of *P. aeruginosa* in plasma in patients with sepsis or bacteremias and thus be able to give a suitable treatment to the patient which allows us to eliminate said infection, this methodology was applied to the analysis of the plasma samples.

Thus, plasma samples were obtained from patients not infected with *P. aeruginosa* and they were grouped to investigate the possible non-specific interferences caused by the matrix. In first place, the plasma samples were treated as described in the experimental section, they were diluted several times with the assay buffer and the different sample dilutions were used to evaluate interferences in the ELISA. Neither the intact plasma nor the hydrolyzed samples significantly interfere in the assay. A 5× dilution with PBST or with the hydrolysis buffer was found to be sufficient to avoid the interferences caused by the sputum components (see table 1). Bearing in mind the dilution factor applied, pyocyanin may be analysed in plasma samples with a LOD of 2.4±0.01 nM (N=2).

The invention claimed is:

1. A conjugate comprising a hapten comprising a mixture of 9-hydroxyphenazine-2-carboxylic acid (I) and 6-hydroxyphenazine-2-carboxylic acid (II)

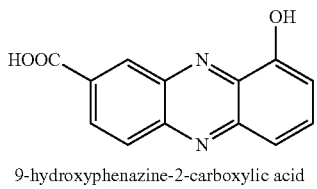

9-hydroxyphenazine-2-carboxylic acid

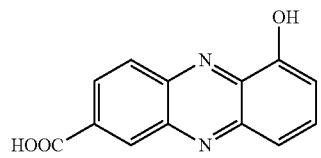

6-hydroxyphenazine-2-carboxylic acid;

and a carrier protein.

2. The conjugate of claim 1, wherein the carrier protein is selected from the group consisting of: horseshoe crab hemocyanin (HCH), bovine serum albumin (BSA), horseradish peroxidase (HRP), ovalbumin (OVA), and conalbumin (CONA).

* * * * *